(12) United States Patent
Thiry et al.

(10) Patent No.: US 7,754,223 B2
(45) Date of Patent: Jul. 13, 2010

(54) *PISCIRICKETTSIA SALMONIS* ANTIGENS AND USE THEREOF

(75) Inventors: Michel Thiry, Trooz (BE); Ingrid Dheur, Ivoz Ramet (BE)

(73) Assignee: Eurogentec SA, Seraing (Ougree) (BE)

( * ) Notice: Subject to any disclaimer, the term of this patent is extended or adjusted under 35 U.S.C. 154(b) by 0 days.

(21) Appl. No.: 10/574,639

(22) PCT Filed: Oct. 1, 2004

(86) PCT No.: PCT/IB2004/003339

§ 371 (c)(1),
(2), (4) Date: Feb. 28, 2007

(87) PCT Pub. No.: WO2005/035558

PCT Pub. Date: Apr. 21, 2005

(65) Prior Publication Data

US 2007/0207165 A1 Sep. 6, 2007

(30) Foreign Application Priority Data

Oct. 7, 2003 (IE) .................................. 2003/0743

(51) Int. Cl.
| A01N 43/04 | (2006.01) |
|---|---|
| A61K 31/70 | (2006.01) |
| A61K 39/02 | (2006.01) |
| C01H 21/04 | (2006.01) |
| C12Q 1/68 | (2006.01) |
| C12P 21/04 | (2006.01) |
| C12N 15/00 | (2006.01) |
| A01N 63/00 | (2006.01) |

(52) U.S. Cl. .................. 424/234.1; 536/23.7; 435/6; 435/71.2; 435/320.1; 424/93.4; 514/44 R

(58) Field of Classification Search ................ None
See application file for complete search history.

(56) References Cited

U.S. PATENT DOCUMENTS

| 5,165,925 | A * | 11/1992 | Leong ................. 424/186.1 |
|---|---|---|---|
| 6,887,989 | B2 | 5/2005 | Simard et al. |
| 2003/0147909 | A1 | 8/2003 | Gonzalez |
| 2003/0166526 | A1 | 9/2003 | Challita-Eid |
| 2004/0086524 | A1 | 5/2004 | Kuzyk |
| 2005/0002946 | A1 | 1/2005 | Kuzyk |

FOREIGN PATENT DOCUMENTS

| CL | 2086-2001 | 8/2001 |
|---|---|---|
| CL | 3110-2001 | 12/2001 |
| CL | 3111-2001 | 12/2001 |
| CL | 3112-2001 | 12/2001 |
| CL | 3113-2001 | 12/2001 |
| CL | 1047-2003 | 5/2003 |
| CL | 1048-2003 | 5/2003 |
| CL | 1049-2003 | 5/2003 |
| EP | 0 712 926 | 5/1996 |
| WO | WO 01/49712 | 7/2001 |
| WO | WO 01/68865 | 9/2001 |
| WO | WO 02/38770 | 5/2002 |

OTHER PUBLICATIONS

Simon., Benjamin.Dissertation Abstracts International, vol. 62/10-B, p. 4363 (abstract citation).*
Morzunov et al. Virus Research. Oct. 1995vol. 38:175-192 .*
Argenton et al, Diseases of Aquatic Organisms, vol. 24:121-127, 1996.*
Gudding et al. Veterinary Immunology and Immunopathology, 72 (1999): 203-212.*
Gerhold et al. BioEssays, vol. 18, No. 12, p. 973-981, 1996.*
Wells et al. Journal of Leukocyte Biology, vol. 61, No. 5, p. 545-550, 1997; Bork. Genome Research 2000, 10:398-400.*
Bork. Genome Research 2000, 10:398-400.*
Greenspan et al. (Nature Biotechnology 7: 936-937, 1999).*
Ellis, R.W. (Chapter 29 of "Vaccines" [Plotkin, S.A. et al. (eds) published by W. B. Saunders company (Philadelphia) in 1988.*
Rollenhagen et al. PNAS, Jun. 8, 2004 101:8739-8744.*
Thacker J Vet Diagn Invest 10:308-311, 1998.*
Stowers et al Infection and Immunity, Dec. 2002, p. 6961-6967.*
Didier et al Veterinary Parasitology 126 (2004) 145-166.*
Lederer et al Infection and Immunity, Feb. 1987, p. 381-387.*
Schade et al Veterinary Parasitology 100 (2001): 63-74.*
Cross et al Veterinary Microbiology 66 (1999):235-243.*
New England Biolabs Catalog 1996/97, p. 111.*
Definition of Vaccine: The Dictionary of Immunology, Herbert et al eds, Academic Press, 1995.*
Harlow et al , Antibodies A Laboratory Manual, Cold Spring Harbor Laboratory Press Inc., 1988, see pp. 23-25, 27-33 and 72-74.*
Greenspan et al, Nature Biotechnology 17:936-937, 1999.*
Colman et al. (Research in Immunology 145: 33-36, 1994.*
Houghten et al. New Approaches to Immunization, Vaccines 86, Cold Spring Harbor Laboratory, p. 21-25, 1986.*

(Continued)

*Primary Examiner*—Robert Mondesi
*Assistant Examiner*—Oluwatosin Ogunbiyi
(74) *Attorney, Agent, or Firm*—Lucas & Mercanti, LLP

(57) ABSTRACT

The present invention discloses novel proteins, e.g., antigens, from *Piscirickettsia salmonis*. The present invention further discloses nucleic acids that encode these proteins. The present invention also discloses the use of the proteins, e.g., antigens, and nucleic acids to prepare vaccines against salmonid rickettsial septicemia (SRS). The present invention further provides recombinant *Yersinia ruckeri* cells to be used to construct vaccines against SRS. The present invention also discloses vaccines that can be used to protect fish from *Piscirickettsia salmonis*, as well as other pathogens. In addition, the present invention discloses methods of using the vaccines of the present invention to protect fish from SRS as well as from other pathogenic diseases.

36 Claims, 2 Drawing Sheets

OTHER PUBLICATIONS

Molling et al. J Mol. Med (1997) 75: 242-246.*
Tighe et al. Immunology Today vol. 19, p. 89-97.*
Dittmer et al Current Opinion in Microbiology vol. 6 Oct. 2003 p. 472-477.*
Jorgensen et al. Developmental and Comparative immunology 25 (2001) 313-32.*
Jones et al (Diseases of Aquatic Organisms vol. 33: 25-31, 1998.*
Definition of infection from American Heritage Dictionary of the English Language, 4th Edition, 2000.*
Jae Hyung An, et al., A Gene Cluster Encoding Malonyl-CoA Decarboxylase . . . , Eur. J. Biochem. vol. 257, pp. 395-402, 1998, XP-002337933.
M.N. Barnes, et al., Purification of *Pisciricicettsia salmonis* and Partial . . . , Diseases of Aquatic Organisms, vol. 33, pp. 33-41, 1998, XP-001029898.
Vitalia Henriquez, et al., An Alternative Efficient Procedure for Purification of the Obligate . . . , Applied and Environmental Microbiology,vol. 69, pp. 6268-6271, 2003, XP001206212.
An, J.H., and Kim, Y.S., A Gene Cluster Encoding Malonyl-CoA . . . , General Description References Comments Links Sequence, XP-002338107.
J.C. Leong, et al., Fish Vaccine Antigens Produced . . . , Dev. Biol. Stand. Basel, Karger, vol. 90, pp. 267-277, 1997 XP-001062656.
Kuzyk, Michael A., Antigenic Characterization of the Salmonid . . . , Infection and Immunity, Dec., pp. 5205-5210, 1996, XP-001029511.
Russmann, Holger, et al., Attenuated Yersinia Pseudotuberculosis . . . , Infection and Immunity, pp. 3463-3472, Jun. 2003, XP-002325391.
Henriquez, Vitalia, et al., An Alternative Efficient Procedure . . . , Applied and Environmental Microbiology, pp. 6268-6271, Oct. 2003, XP001206212.
Valenzuela, P., et al., "Sequence and Applications of the *Pisciricktttsia salmonis* Genome", Biological Research, vol. 34, pp. 3-4, 2001, XP-002325385.
Henriquez, V B., Improved Purification of HTE Obligate Intracellular . . . , XP-002325615 meeting abstract 102nd general meeting of the American Society Microbiology, Salt Lake City, Utah May 19-23, 2002.
Miquel, Alvaro, et al., Immunoresponse of COHO Salmon Immunized . . . , Biol Res., vol. 36, pp. 313-323, 2003, XP-002325386.
Wilhelm, Vivian, et al., The Complete Sequence of the Mitochondrial Genome . . . , Bio Res. vol. 36, pp. 223-231, 2003, XP009046676.

* cited by examiner

PISCIRICKETTSIA SALMONIS ANTIGENS AND USE THEREOF

CROSS-REFERENCE TO RELATED APPLICATIONS

This patent application claims the benefit of priority from Irish Patent Application No. 2003/0743 filed Oct. 7, 2003 through PCT Application Ser. No. PCT/IB2004/003339 filed Oct. 1, 2004 the contents of which are incorporated herein by reference.

BACKGROUND OF THE INVENTION

1. Field of Invention

The present invention relates to novel antigens from *Piscirickettsia salmonis*. The present invention also pertains to the nucleic acids that encode these antigens. The present invention further relates to a process of preparing a vaccine against salmonid rickettsial septicemia (SRS) using the antigens or nucleic acids. The present invention also relates to bacterins and viral antigens that can be combined to form a vaccine against SRS. The present invention also pertains to vaccines for preventing SRS, as well as preventing other bacterial and/or viral infections in fish.

2. Background

Salmonid rickettsial septicemia (SRS), also known as piscirickettsiosis, is a fatal disease in salmonids. Although the etiological agent for SRS was identified in the late 1980's as *Piscirickettsia salmonis*, antibiotics proved to be an unsuccessful treatment, due, at least in part, to the intracellular nature of this bacterium [Bravo and Campos, *FHS/AFS Newsl.* 17:3 (1989); U.K. Patent Application 2 356 632]. As a consequence of the lack of a viable treatment, millions of farmed salmon die of SRS each year just in southern Chile alone [Smith et al., *Dis. Aquat. Organ.* 37(3):165-172 (1999)]. In addition, recent reports demonstrate a link between *Piscirickettsia*-like bacteria and disease syndromes in non-salmonid fish [see, Mauel and Miller, *Veterin. Microbiol.* 87(4):279-289 (2002)].

The Salmonidae family (salmonids) includes salmon, trout, char, and whitefish. Salmonids serve both as a food source and as a game fish. Moreover, in countries such as Chile, Norway, Canada, the United Kingdom, Ireland, and the United States, salmonids have become an important commercial product due, at least in part, to the ability of fish farmers to artificially spawn, incubate and raise the salmonids in captivity.

Unlike fish originating in the wild, those raised in captivity are amenable to prophylactic treatments such as vaccination. However, to date, no safe and effective vaccine against *Piscirickettsia salmonis* has been forthcoming, though others have recently suggested potential vaccines, such as one based on a specific *Piscirickettsia salmonis* antigen, a 17 kDa lipoprotein OspA [U.K. Patent Application 2 356 632; see also WO 01/68865 A2].

In addition, to *Piscirickettsia salmonis* other pathogens are known to cause disease in farmed fish, including salmon. One such pathogen is the Infectious Pancreatic Necrosis virus (IPN virus), which is an unenveloped, icosahedral, bisegmented dsRNA virus. The IPN virus contains one main structural protein, VP2 (52 kDa) and three additional proteins, VP1 (90 k Da), VP3 (30 kDa) and VP4 (28 kDa). VP2 is the main protein of the outer capsid and is therefore immunologically important in recognition and bonding of the virus. VP1 is thought to be a polymerase, whereas VP3 and VP4 are internal proteins. VP4 is believed to correspond to a form of VP3 fragment formed during viral differentiation [see, WO 02/38770 A1, the contents of which are hereby incorporated by reference in their entireties]. Nucleotide and amino acid sequences for VP2 and VP3 have been determined [see, Havarstein et al., *J. Gen. Virol.* 71:299-308 (1990); Pryde et al., *Archives of Vir.* 129:287-293 (1992)].

Therefore, there is a need to provide safe and effective vaccines against *Piscirickettsia salmonis*. In addition, there is a need to identify new antigens from *Piscirickettsia salmonis* that can be used in such vaccines.

Furthermore, there is a need to obtain nucleic acids that encode such antigens. In addition, there is a need to provide methods of vaccinating fish to protect them from *Piscirickettsia salmonis* and *Piscirickettsia*-like bacteria. Furthermore, there is a need to provide vaccines that can protect fish against *Piscirickettsia salmonis* and other unrelated pathogens, such as IPN virus.

The citation of any reference herein should not be construed as an admission that such reference is available as "prior art" to the instant application.

SUMMARY OF THE INVENTION

The present invention provides safe and effective vaccines to protect fish against *Piscirickettsia salmonis* infections. In addition, the present invention provides methods of vaccinating fish to protect them from *Piscirickettsia salmonis* and *Piscirickettsia*-like bacteria. Moreover, the present invention provides vaccines that can protect vaccinated fish from *Piscirickettsia salmonis* and other unrelated pathogens, such as IPN virus. Methods of making the vaccines of the present invention are also provided.

The present invention further provides specific antigens from *Piscirickettsia salmonis* that can be used in vaccines. In addition, the present invention provides nucleic acids that encode these antigens. Furthermore, the present invention provides nucleic acid probes, PCR primers and antibodies that can be used to identify these antigens or the nucleic acids that encode the antigens. In addition, the present invention provides recombinant bacterial cells that encode the antigens, as well as the corresponding bacterins prepared from the bacterial cells.

In one aspect of the present invention, an antigen from *Piscirickettsia salmonis* is provided. In a particular embodiment, the antigen from *Piscirickettsia salmonis* is an isolated $^{Ps}$p45 protein. The present invention further provides a recombinant $^{Ps}$p45 protein. Preferably, when an antigen or antigenic fragment thereof is placed into a vaccine, the recipient of the vaccine receives protection from *Piscirickettsia salmonis*.

The present invention further provides a $^{Ps}$p45 protein that comprises an amino acid sequence that has at least 70% identity with the amino acid sequence of SEQ ID NO: 2 and/or SEQ ID NO: 4. In a particular embodiment, the $^{Ps}$p45 protein comprises an amino acid sequence that has at least 85% identity with the amino acid sequence of SEQ ID NO: 2 and/or SEQ ID NO: 4. In another embodiment, the $^{Ps}$p45 protein comprises an amino acid sequence that has at least 95% identity with the amino acid sequence of SEQ ID NO: 2 and/or SEQ ID NO: 4. Preferably, differences in amino acid sequences of the $^{Ps}$p45 proteins of the present invention are due to variations found in different strains of *Piscirickettsia salmonis*. The present invention further provides antigenic fragments of all of the variant $^{Ps}$p45 proteins.

In a particular embodiment the $^{Ps}$p45 protein of the present invention comprises the amino acid sequence of SEQ ID NO: 2 and/or SEQ ID NO: 4. In a related embodiment, the $^{Ps}$p45 protein comprises the amino acid sequence of SEQ ID NO: 2 and/or SEQ ID NO: 4 comprising a conservative amino acid substitution. In another embodiment the $^{Ps}$p45 protein consists essentially of the amino acid sequence of SEQ ID NO: 2 and/or SEQ ID NO: 4. In still another embodiment, the $^{Ps}$p45 protein consists essentially of the amino acid sequence of SEQ ID NO: 2 and/or SEQ ID NO: 4 comprising a conservative amino acid substitution. In yet another embodiment the $^{Ps}$p45 protein consists of the amino acid sequence of SEQ ID NO: 2 and/or SEQ ID NO: 4. In still another embodiment, the $^{Ps}$p45 protein consists of the amino acid sequence of SEQ ID NO: 2 and/or SEQ ID NO: 4 comprising a conservative amino acid substitution. Other antigens and/or polypeptides provided by the present invention include isolated and/or recombinant proteins that comprise an amino acid sequence of SEQ ID NOs: 6, 8, 10, 12, 14, 16, or 18.

The present invention also provides antigenic fragments of the antigens of the present invention. In a particular embodiment, the antigenic fragment is a portion of a $^{Ps}$p45 protein. In one embodiment the antigenic fragment is a portion of a $^{Ps}$p45 protein that comprises an amino acid sequence that has at least 70% identity with the amino acid sequence of SEQ ID NO: 2 and/or SEQ ID NO: 4. In yet another embodiment of this type, the antigenic fragment is a portion of a $^{Ps}$p45 protein that has the amino acid sequence of SEQ ID NO: 2 and/or SEQ ID NO: 4. In a related embodiment, the antigenic fragment is a portion of a $^{Ps}$p45 protein that has the amino acid sequence of SEQ ID NO: 2 and/or SEQ ID NO: 4 comprising a conservative amino acid substitution.

The present invention further provides recombinant polypeptides that comprise an antigenic fragment of the antigens of the present invention. In a particular embodiment, the recombinant polypeptide comprises the amino acid sequence of an antigenic fragment of the $^{Ps}$p45 protein as described above.

The present invention also provides chimeric proteins that comprise the antigens and corresponding antigenic fragments of the present invention. In one such embodiment, a chimeric protein comprises the amino acid sequence of a $^{Ps}$p45 protein. In another embodiment, a chimeric protein comprises the amino acid sequence of an antigenic fragment of a $^{Ps}$p45 protein. In a particular embodiment, a chimeric protein comprises the amino acid sequence of a $^{Ps}$p45 protein in which the natural signal peptide has been replaced by an alternative signal peptide.

In addition, antibodies to all of the antigens and antigenic fragments thereof of the present invention also are provided by the present invention. In a particular embodiment of this type, the present invention provides an antibody to the $^{Ps}$p45 protein. In a particular embodiment of this type, the antibody is raised against a $^{Ps}$p45 protein of the present invention or an antigenic fragment thereof. In one such embodiment, the antibody is a polyclonal antibody. In another embodiment, the antibody is a monoclonal antibody. In yet another embodiment, the antibody is a chimeric antibody. In a particular embodiment, an antibody of the present invention is raised against a $^{Ps}$p45 protein that comprises the amino acid sequence of SEQ ID NO: 2 and/or SEQ ID NO: 4. In a related embodiment, the antibody is raised against a $^{Ps}$p45 protein that comprises the amino acid sequence of SEQ ID NO: 2 and/or SEQ ID NO: 4 that comprises a conservative amino acid substitution. It is preferable that the antibody recognizes a specific epitope of the $^{Ps}$p45 protein. In a related embodiment, the present invention provides a fragment of an antibody of the present invention.

The present invention further provides isolated and/or recombinant nucleic acids that encode each of the antigens and/or polypeptides of the present invention. The present invention thus provides isolated and/or recombinant nucleic acids that encode the amino acid sequences of SEQ ID NOs: 2, 4, 6, 8, 10, 12, 14, 16, and/or 18. Moreover, the present invention provides isolated and/or recombinant nucleic acids that comprise the nucleotide sequences of SEQ ID NOs: 1, 3, 5, 7, 9, 11, 13, 15, 17, and/or 19, and/or fragments thereof. In one such embodiment, the nucleic acid comprises two or more of these nucleotide sequences.

The present invention also provides nucleic acids that encode each of the antigenic fragments of the present invention. In addition, the present invention further provides nucleic acids that encode each of the corresponding chimeric proteins. All of the nucleic acids of the present invention can further comprise heterologous nucleotide sequences. The present invention further provides nucleotide probes and primers for the nucleic acids of the present invention.

The present invention further provides a nucleic acid that hybridizes to a nucleotide sequence of the present invention, e.g., a cDNA consisting of the nucleotide sequence of SEQ ID NO: 1 and/or SEQ ID NO: 3. In a particular embodiment the nucleic acid comprises the entire coding sequence of a protein of the present invention, e.g., the $^{Ps}$p45 protein. Appropriate hybridization conditions are provided below.

In one embodiment a nucleic acid comprises at least 12 nucleotides. In another embodiment the nucleic acid comprises at least 18 nucleotides. In yet another embodiment the nucleic acid comprises at least 24 nucleotides. In still another embodiment the nucleic acid comprises at least 36 nucleotides. In yet another embodiment the nucleic acid comprises at least 48 nucleotides. In still another embodiment the nucleic acid comprises at least 72 nucleotides.

In a particular embodiment, the present invention provides an isolated and/or recombinant nucleic acid encoding a $^{Ps}$p45 protein that comprises an amino acid sequence that has at least 70% identity with the amino acid sequence of SEQ ID NO: 2 and/or SEQ ID NO: 4. In a preferred embodiment, the nucleic acid encodes a $^{Ps}$p45 protein that comprises the amino acid sequence of SEQ ID NO: 2 and/or SEQ ID NO: 4. In a more preferred embodiment of this type, the nucleic acid comprises the nucleotide sequence of SEQ ID NO: 1 and/or SEQ ID NO: 3. In yet another embodiment, a nucleic acid of the present invention encodes a chimeric protein that comprises the amino acid sequence of an antigenic fragment of a $^{Ps}$p45 protein.

The present invention also provides vectors that can comprise one or more of the nucleic acids of the present invention. In a specific embodiment, the vector comprises the nucleotide sequences of SEQ ID NOs: 5, 7, 9, 11, 13, 15, 17, and 19, or fragments thereof. Preferably, one or more of the nucleic acids of the present invention are operatively linked to a transcriptional control sequence in an expression vector. Host cells comprising the vectors (including expression vectors) are also part of the present invention. In one embodiment, the host cell is a gram negative bacterium. In one such embodiment of this type, the host cell is an *Escherichia coli* cell. In a preferred embodiment, the host cell is a *Yersinia ruckeri* cell.

In addition, the present invention provides methods for producing a polypeptide comprised by the above-mentioned host cells. One such method comprises culturing the host cell that expresses a nucleic acid encoding the polypeptide of the present invention, e.g., an antigen or antigenic fragment thereof, thereby producing the polypeptide. Methods for purifying and/or obtaining the resulting recombinant proteins are also included in the present invention, e.g., the purified recombinant antigens and antigenic fragments.

The present invention further provides recombinant bacterial cells. In one such embodiment the recombinant bacterial cell is a *Yersinia ruckeri* cell to having the BCCM accession No. LMG P-22044. In another embodiment the recombinant bacterial cell is a *Yersinia ruckeri* cell having the BCCM accession No. LMG P-22511.

The present invention also provides immunogenic compositions comprising the proteins, and/or antigenic fragments, and/or recombinant host cells, and/or bacterins of the present invention.

In still another aspect, the present invention provides vaccines. The vaccines of the present invention can comprise any of the immunogenic compositions of the present invention. Preferred vaccines protect fish against SRS, either alone or in multivalent vaccines that may also protect against other pathogens. In a related embodiment, a vaccine is a naked DNA vaccine that comprises a recombinant DNA vector that comprises a nucleic acid encoding an antigen, or an antigenic fragment thereof, of the present invention Any fish may be the recipient of the vaccines of the present invention. Examples of recipient fish are listed below. In a particular embodiment, the fish is a teleost. In a preferred embodiment, the teleost is a salmonid. In a more preferred embodiment the salmonid is a salmon. In one such embodiment the salmon is a *Salmo salar* (Atlantic salmon). In another embodiment the salmon is an *Oncorhynchus kisutch* (coho salmon). In yet another embodiment the salmonid is an *Oncorhynchus mykiss* (rainbow trout).

In a particular embodiment, a vaccine comprises and/or encodes a $^{Ps}$p45 protein, or an antigenic fragment thereof. In another embodiment, the vaccine comprises and/or encodes one or more antigens and/or proteins that comprise an amino acid sequence of SEQ ID NOs: 2, 4, 6, 8, 10, 12, 14, 16, or 18, and/or fragments thereof. In yet another embodiment the vaccine comprises a bacterin of a *Yersinia ruckeri* cell having the BCCM accession No. LMG P-22044. In still another embodiment the vaccine comprises a bacterin of a *Yersinia ruckeri* cell having the BCCM accession No. LMG P-22511. In yet another embodiment the vaccine comprises a bacterin of a *Yersinia ruckeri* cell having the BCCM accession No. LMG P-22511 along with a bacterin of a *Yersinia ruckeri* cell having the BCCM accession No. LMG P-22044. Preferably, such vaccines provide fish protection from SRS.

In another embodiment, a vaccine of the present invention further comprises and/or encodes one or more antigens obtained from an Infectious Pancreatic Necrosis (IPN) virus. These recombinant proteins are preferably expressed by transformed yeast, *Pichia pastoris*. In one such embodiment, the antigen obtained from the IPN virus is the VP2 var protein or antigenic fragment thereof. In another embodiment the antigen obtained from the IPN virus is the VP3 protein or antigenic fragment thereof. In a particular embodiment, the vaccine comprises both the VP2 var protein or antigenic fragment thereof and the VP3 protein or antigenic fragment thereof.

In one embodiment, an antigen is the portion of the VP2 var protein obtained from the transformed *Pichia pastoris* cell, BCCM Accession No. IHEM 20069. In another embodiment of this type, an antigen is the portion of the VP2 var protein obtained from the transformed *Pichia pastoris* cell, BCCM Accession No. IHEM 20070. In still another embodiment, an antigen is the portion of the VP3 protein obtained from the transformed *Pichia pastoris* cell, BCCM Accession No. IHEM 20071. In yet another embodiment, an antigen is the portion of the VP3 protein obtained from the transformed *Pichia pastoris* cell, BCCM Accession No. IHEM 20072. In a particular embodiment the vaccine comprises antigens from transformed *Pichia pastoris* cells, BCCM Accession No. IHEM 20069 and BCCM Accession No. IHEM 20071. In another embodiment the vaccine comprises antigens from transformed *Pichia pastoris* cells. BCCM Accession No. IHEM 20070, and BCCM Accession No. IHEM 20072.

In still another embodiment a vaccine of the present invention comprises one or more antigens obtained from *Aeromonas salmonicida*. In a particular embodiment, the *Aeromonas salmonicida* comprising the antigens is prepared from a culture grown under iron-depleted conditions. In another embodiment, the *Aeromonas salmonicida* comprising the antigens is prepared from a culture grown under iron-supplemented conditions. In a particular embodiment, two sets of *Aeromonas salmonicida* antigens are employed in the vaccine, one set from a culture grown under iron-depleted conditions, the other set from a culture grown under iron-supplemented conditions. In a particular embodiment, a multivalent vaccine comprises antigens from *Piscirickettsia salmonis*, IPN, and *Aeromonas salmonicida.*

The present invention also provides methods of protecting a fish from salmonid rickettsial septicemia (SRS), or SRS along with one or more other pathogenic disease(s) through the vaccination of the fish with a vaccine of the present invention. In a particular embodiment the other disease is Infectious Pancreatic Necrosis. In another embodiment the other disease is furunculosis. In still another embodiment the method of protecting the fish includes protecting against SRS, Infectious Pancreatic Necrosis, and furunculosis (caused by *Aeromonas salmonicida*).

The vaccines of the present invention can be administered by any method. In one embodiment a vaccine of the present invention is administered by immersion. In another embodiment a vaccine of the present invention is administered by injection. In yet another embodiment a vaccine of the present invention is administered by oral administration.

In addition, related booster vaccines are also provided by the present invention. The administration of a given booster vaccine is preferably performed through oral administration.

In another aspect of the present invention, methods are provided for expressing recombinant bacterial surface antigens that are otherwise extremely difficult to express. In one such embodiment, an enteric bacterium that is not present in humans (e.g., a *Yersinia ruckeri* cell) is used as a recombinant vector to express a surface antigen (e.g., an outer membrane protein) from an intracellular pathogen. Preferably, the recombinant bacterial vector is used in a vaccine. In a preferred embodiment of this type, the recombinant bacterium is inactivated (i.e., a bacterin). Heretofore, it was neither known nor expected that in fish, the resulting recombinant bacterin would be much more antigenic than a corresponding recombinant non-enteric bacterin.

Therefore, the present invention provides vaccines for use in non-human animals to protect against intracellular pathogens. The present invention further provides methods of vaccinating the non-human animal comprising administering the vaccine to the non-human animal. Methods of making the vaccines are also provided.

One such vaccine comprises a recombinant enteric bacterium encoding a surface antigen, or antigenic fragment thereof, of the intracellular pathogen. In a preferred embodiment of this type, the surface antigen is an outer membrane protein. In a particular embodiment the enteric bacterium is inactivated. In a preferred embodiment, the enteric bacterium is *Yersinia ruckeri.*

Preferably the non-human animal is a fish. More preferably the fish is a teleost. Representative teleosts are listed below. In a preferred embodiment of this type the teleost is a salmonid.

In one such embodiment, the salmonid is a *Salmo salar* (Atlantic salmon). In another embodiment the salmonid is an *Oncorhynchus kisutch* (coho salmon). In yet another embodiment the salmonid is an *Oncorhynchus mykiss* (rainbow trout).

Accordingly, it is a principal object of the present invention to provide a vaccine that protects salmonids against SRS.

It is a further object of the present invention to provide a vaccine that protects fish from salmonid rickettsial septicemia (SRS) and Infectious Pancreatic Necrosis (IPN).

It is a further object of the present invention to provide an effective way of to protect against assorted fish infections by providing a multivalent vaccine.

It is a further object of the present invention to provide a protocol that can lead to the successful vaccination of fish in captivity.

It is a further object of the present invention to provide a DNA construct that encodes the $^{Ps}$p45 protein or variant thereof.

It is a further object of the present invention to provide a polypeptide having an amino acid substitution SEQ ID NO: 2, or an antigenic fragment thereof.

It is a further object of the present invention to provide a polypeptide having an amino acid substitution SEQ ID NO: 4, or an antigenic fragment thereof.

It is a further object of the present invention to provide a recombinant subunit vaccine against SRS.

It is a further object of the present invention to provide inactivated recombinant bacterial vectors encoding specific antigens to be used in vaccines against SRS.

It is a further object of the present invention to provide recombinant non-human enteric bacterial vectors to be used to express an outer membrane protein from a different intracellular pathogen.

These and other aspects of the present invention will be better appreciated by reference to the following drawings and Detailed Description.

DETAILED DESCRIPTION OF THE INVENTION

Figure 1:
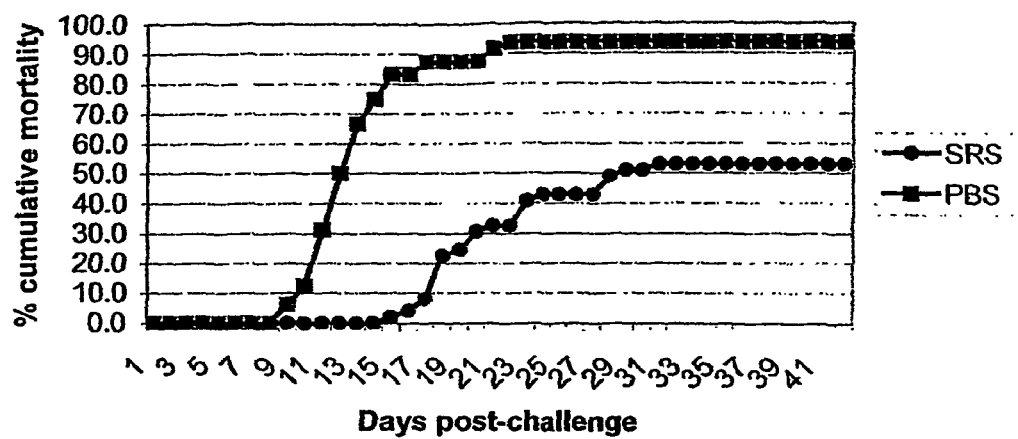
FIG. 1 shows the mortality due to SRS beginning 9 days post-challenge in the PBS control group, and 15 days post-challenge in the SRS vaccinated group (see Example 7 below).

The present invention provides vaccines to protect fish against SRS. The present invention further provides vaccines that protect fish against SRS and one or more other pathogenic diseases. In addition, booster vaccines are also provided by the present invention. The vaccines of the present invention (including booster vaccines) can be administered to fish by a number of means including by immersion, by injection and/or through oral administration.

The present invention also provides specific antigens from *Piscirickettsia salmonis*. Though these antigens may be placed into a vaccine in any number of forms (e.g., as a recombinant protein or in a DNA vaccine) the preferred embodiment is as an expressed protein in an inactivated recombinant gram negative bacterium.

One preferred antigen of the present invention is the $^{Ps}$p45 protein. The coding sequence for $^{Ps}$p45 protein is contained by a recombinant Chilean strain of *Yersinia ruckeri* that has been deposited (BCCM accession No. LMG P-22044). The nucleotide coding sequence of the $^{Ps}$p45 protein within the deposited recombinant *Yersinia ruckeri* is SEQ ID NO: 1 (see Example 1 below where it is depicted). The amino acid sequence of the $^{Ps}$p45 protein within the deposited recombinant *Yersinia ruckeri* is SEQ ID NO: 2. A putative signal peptide in SEQ ID NO: 2 is depicted by underlining in the amino acid sequence below. As is apparent from the depiction of the amino acid sequence, the cleavage site is in between two alanine residues at positions 22 and 23, respectively. This signal peptide can be replaced by alternative signal peptides to enhance secretion of the $^{Ps}$p45 protein and such chimeric proteins are included in the present invention.

As denoted herein, the full length $^{Ps}$p45 protein has the amino acid sequence indicated below, denoted as SEQ ID NO: 2. The $^{Ps}$p45 protein lacking the signal peptide (i.e., lacking the amino-terminal 22 amino acids of SEQ ID NO: 2) has the amino acid sequence of SEQ ID NO: 4. SEQ ID NO: 3 is the nucleotide coding sequence of the $^{Ps}$p45 protein lacking the signal peptide.

```
SEQ ID NO: 2:
  1 MKVKMIVAAV AVAGLTATAA NAADNGKLQL QINQLKAQHT QLQQQVANLQ

51 GQGQTTGAVH VGAVGGELIS ENNYDGRGLD LLKSLAKAGS NAPLLTIGGT

101 LEADAQMNRN GNVGSGSTSG DPSGLNYTDG TSSSAFYLDT ARIDILAHVN

151 DWVNGEISYD LNGDSGLHTG SLLVGNLNQL PVYGQIGKFY PDAGLFELAS

201 DDVYSSSLVK RYFRPDAQNG ASVGFYKAGL HTSLTAFKTS APQANAANYN

251 QATSDWSAQA DYTFNAGQVN ATIGAGYLSN MVNTNDSFTA TGAGTGTQKD

301 RLPMANVSAK IGFGPFEALA TYAQTLKGLA NTTGGTTKLK AFDLEGAYHF

351 QAVKPMTVML GYSRTYGFDK VGPVDQFIDG NTAITINNKK DQWLLGVNSE

401 VFKNTTVGLE YARVGQLDST GTDTNRYNVL TADMTVKF*
```

The present invention also provides a second deposited, recombinant *Yersinia ruckeri* cell (BCCM accession No. LMG P-22511). In a particular embodiment of the present invention the SRS vaccine comprises bacterins of the deposited, recombinant *Yersinia ruckeri* cells (BCCM accession Nos. LMG P-22511, along with LMG P-22044).

These recombinant *Yersinia ruckeri* cells were all deposited with the:
Belgian Coordinated Collections of Microorganisms (BCCM)
Laboratorium voor Microbiologie—Bacteriënverzameling (LMG)
Universiteit Gent
K.L. Ledeganckstraat 35
B-9000 Gent, Belgium
  Strain Name: *Yersinia ruckeri* 224/pGEM5ZF+145 kDa/S
    BCCM accession No. LMG P-22044, deposited on Sep. 11, 2003.
  Strain Name: *Yersinia ruckeri* 224/pGEM5ZF+175 kDa
    BCCM accession No. LMG P-22511, deposited on May 27, 2004.

The present invention also provides vaccines against SRS and IPN (SRS/IPN vaccines) that further comprise one or more antigens obtained from an Infectious Pancreatic Necrosis (IPN) virus. These recombinant proteins are preferably expressed by transformed yeast, *Pichia pastoris*.

In one such embodiment, the antigen obtained from the IPN virus is the VP2 var protein or an antigenic fragment thereof. In a particular embodiment, the antigen is the VP2 var protein obtained from the transformed *Pichia pastoris* cell, BCCM Accession No. IHEM 20069 and/or from the transformed *Pichia pastoris* cell, BCCM Accession No. IHEM 20070. In another embodiment, the antigen obtained from the IPN virus is the VP3 protein or an antigenic fragment thereof. In a particular embodiment of this type, the antigen is the VP3 protein obtained from the transformed *Pichia pastoris* cell, BCCM Accession No. IHEM 20071 and/or from the transformed *Pichia pastoris* cell BCCM Accession No. IHEM 20072. In one embodiment of the present invention, the SRS/IPN vaccine comprises at least one VPvar antigen and one VP3 antigen.

Four recombinant *Pichia pastoris* yeast cells were deposited with the:
Belgian Coordinated Collections of Microorganisms (BCCM)
Institut Scientifique de la Santé Publique—Louis Pasteur (IHEM)
Section mycologie
J. Wytsmanstraat 14 Rue J. Wytsman
B-1050 Brussels, Belgium
  All four of these deposits were all made on Sep. 11, 2003.
  Strain name: *Pichia pastoris* GS115/pPICZaB/VP2var/MUT+ 46
    BCCM Accession No. IHEM 20069
    This recombinant cell encodes the VP2 var *antigen* and human serum antigen (HSA).
  Strain name: *Pichia pastoris* SMD1168/pPICZaB/VP2 367.5
    BCCM Accession No. IHEM 20070
    This recombinant cell encodes the VP2 var antigen without HSA.
  Strain name: *Pichia pastoris* KM71/pPICZaB/VP3/MUTs 30:11
    BCCM Accession No. IHEM 20071
    This recombinant cell encodes the VP3 antigen with HSA.
  Strain name: *Pichia pastoris* GS115/pPICZaB/VP3 112.15
    BCCM Accession No. IHEM 20072
    This recombinant cell encodes the VP3 antigen without HSA.

As used herein the following terms shall have the definitions set out below:

As used herein the term "$^{Ps}$p45 protein" denotes a *Piscirickettsia salmonis* protein that is approximately 45,000 daltons. The specific full-length $^{Ps}$p45 protein exemplified herein has the amino acid sequence of SEQ ID NO: 2, and is further characterized in Example 1 below. The corresponding $^{Ps}$p45 protein lacking its twenty-two amino acid signal peptide has the amino acid sequence of SEQ ID NO: 4. The full-length $^{Ps}$p45 protein is encoded by the nucleic acid sequence of SEQ ID NO: 1. The recombinant $^{Ps}$p45 protein is encoded by the recombinant *Yersinia ruckeri* cell having the BCCM accession No. LMG P-22044. The cells were deposited on the date of Sep. 11, 2003 with:

The Belgian Coordinated Collections of Microorganisms (BCCM) at the address provided above. A general address for the BCCM is:
Prime Minister's Services
Federal Office for Scientific, Technical and Cultural Affairs (OSTC)
Rue de la Science 8
B-1000 Brussels Belgium As used herein the term "polypeptide" is used interchangeably with the term "protein" and is further meant to encompass peptides. Therefore, as used herein, a polypeptide is a polymer of two or more amino adds joined together by peptide linkages. Preferably, a polypeptide is a polymer comprising twenty or more amino acid residues joined together by peptide linkages, whereas a peptide comprises two to twenty amino acid residues joined together by peptide linkages.

As used herein a polypeptide "consisting essentially of" or that "consists essentially of" a specified amino acid sequence is a polypeptide that (i) retains an important characteristic of the polypeptide comprising that amino acid sequence, e.g., the antigenicity of at least one epitope of the $^{Ps}$p45 protein, and (ii) further comprises the identical amino acid sequence, except it consists of plus or minus 10% (or a lower percentage), and preferably plus or minus 5% (or a lower percentage) of the amino acid residues. In a particular embodiment, additional amino acid residues included as part of the polypeptide are part of a linked Tag, such as a C-terminal His$_6$ Tag.

A molecule is "antigenic" when it is capable of specifically interacting with an antigen recognition molecule of the immune system, such as an immunoglobulin (antibody) or T cell antigen receptor. An antigenic polypeptide (and/or fragment of the polypeptide) contains at least 6, and preferably at least 12 or more amino acid residues. An antigenic portion of a molecule can be that portion that is immunodominant for recognition by an antibody or a T cell receptor, and/or it can be a portion used to generate an antibody to the molecule by conjugating an immunogenic portion of the antigen to a carrier molecule for immunization. A molecule that is antigenic need not be itself immunogenic, i.e., capable of eliciting an immune response without a carrier.

As used herein the term "antigenic fragment" in regard to a particular protein is a fragment of that protein that is antigenic. For example, an antigenic fragment of the $^{Ps}$p45 protein is a fragment of the $^{Ps}$p45 protein that is antigenic. As used herein, an antigenic fragment" of the $^{Ps}$p45 protein, for example, can be any fragment of the $^{Ps}$p45 protein, including large fragments that are missing as little as a single amino acid from the full length protein. In a particular embodiment an antigenic fragment of the $^{Ps}$p45 protein contains between 12 and 200 amino acid residues. In addition, an antigenic fragment of a given protein can be obtained by a recombinant source, from a protein isolated from natural sources, or through chemical synthesis. Moreover, an antigenic fragment can be obtained following the proteolytic digestion of a protein or a fragment thereof, through recombinant expression, or alternatively, it can be generated de novo, e.g., through peptide synthesis.

As used herein, a multivalent vaccine is a vaccine that comprises two or more different antigens. In a particular embodiment of this type, the multivalent vaccine stimulates the immune system of the recipient against two or more different pathogens. Specific multivalent vaccines are exemplified below.

As used herein the term "chimeric" protein is meant to include fusion proteins. "Chimeric" $^{Ps}$p45 proteins of the present invention, for example, comprise at least a portion of a non-$^{Ps}$p45 polypeptide joined via a peptide bond to at least a portion of a $^{Ps}$p45 protein. Chimeric proteins can have additional structural, regulatory, and/or catalytic properties. As used herein a chimeric protein can contain multiple additions to at least a portion of a given protein, e.g., a chimeric $^{Ps}$p45 protein can comprise both a $His_6$ Tag and an alternative signal sequence. In a particular embodiment the chimeric protein functions as a means of detecting and/or isolating the polypeptide or fragment thereof after a recombinant nucleic acid encoding the given protein or antigenic fragment thereof is expressed. Non-$^{Ps}$p45 amino acid sequences, for example, are preferably either amino- or carboxy-terminal to the $^{Ps}$p45 sequence.

As used herein one amino acid sequence is 100% "identical" to a second amino acid sequence when the amino acid residues of both sequences are identical. Accordingly, an amino acid sequence is 50% "identical" to a second amino acid sequence when 50% of the amino acid residues of the two amino acid sequences are identical. The sequence comparison is performed over a contiguous block of amino acid residues comprised by a given protein, e.g., the $^{Ps}$p45 protein, or a portion of the polypeptide being compared. In a particular embodiment, selected deletions or insertions that could otherwise alter the correspondence between the two amino acid sequences are taken into account.

As used herein, DNA and protein sequence percent identity can be determined using C, MacVector 6.0.1, Vector NTI (Informax, Inc. MD), Oxford Molecular Group PLC (1996) and the Clustal W algorithm with the alignment default parameters, and default parameters for identity. These commercially available programs can also be used to determine sequence similarity using the same or analogous default parameters. Alternatively, an Advanced Blast search under the default filter conditions can be used, e.g., using the GCG (Genetics Computer Group, Program Manual for the GCG Package, Version 7, Madison, Wis.) pileup program using the default parameters.

As used herein a "nucleic acid" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. When referring to a nucleic acid that is double stranded both the "sense" strand and the complementary "antisense" strand are intended to be included. Thus a nucleic acid that is hybridizable to SEQ ID NO: 1, for example, can be either hybridizable to the "sense" strand of SEQ ID NO: 1, which is particularly listed in the SEQUENCE LISTING, or to the "antisense" strand which can be readily determined from that SEQUENCE LISTING.

A DNA "coding sequence" is a double-stranded DNA sequence that is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which can then be trans-RNA spliced, when and where appropriate, and translated into the protein encoded by the coding sequence.

A nucleic acid sequence is "operatively linked" to an expression control sequence when the expression control sequence controls or regulates the transcription and translation of that nucleic acid sequence. The term operatively linked includes having an appropriate start signal.

A "heterologous nucleotide sequence" as used herein is a nucleotide sequence that is added by recombinant methods to a nucleotide sequence encoding a polypeptide of the present invention or encoding a fragment (i.e., an antigenic fragment) thereof, to form a nucleic acid that is not naturally formed in nature. Such nucleic acids can encode chimeric proteins. In addition, as used herein, a heterologous nucleotide sequence need not be a single contiguous nucleotide sequence, but can include multiple non-contiguous nucleotide sequences that have been combined with a nucleotide sequence encoding a polypeptide of the present invention, or a portion thereof. A heterologous nucleotide sequence can comprise non-coding sequences including restriction sites, regulatory sites, promoters and the like. In still another embodiment the heterologous nucleotide can function as a means of detecting a nucleotide sequence of the present invention. The present invention provides heterologous nucleotide sequences that when combined with nucleotide sequences encoding a polypeptide of the invention or a fragment thereof, are necessary and sufficient to encode all of the chimeric proteins of the present invention. In a particular embodiment, the polypeptide is the $^{Ps}$p45 protein.

As used herein, a bacterium (or bacterin) is said to be "recombinant" when it has been purposely manipulated to comprise one or more nucleic acids that are not naturally contained by that bacterium (or bacterin).

The phrase "binding to" in regard to a ligand binding to a polypeptide (e.g., antibody-antigen complex) is used herein to include any or all such specific interactions that lead to a protein-ligand binding complex. This can include processes such as covalent, ionic (electrostatic and/or charged), hydrophobic and hydrogen bonding, but does not include non-specific associations such solvent preferences.

As used herein a "small organic molecule" is an organic compound [or organic compound complexed with an inorganic compound (e.g., metal)] that has a molecular weight of less than 3 kDa.

As used herein the terms "approximately" and "about" are used to signify that a value is within twenty percent of the indicated value i.e., an amino acid sequence containing "approximately" 400 amino acid residues can contain between 320 and 480 amino acid residues.

As used herein the unit "days" denotes the number of days of incubation following the vaccination of a fish, multiplied by the average temperature in ° C. for that incubation.

Nucleic Acids Encoding the Polypeptides of the Present Invention

A nucleic acid, such as a cDNA, that encodes a polypeptide of the present invention, can be used to generate recombinant bacterial host cells that express a protein and/or antigen of the present invention, e.g., the $^{Ps}$p45 protein. Such recombinant host cells can be inactivated, i.e., converted to bacterins, and used in immunogenic compositions such as vaccines.

In addition, obtaining and/or constructing a DNA that encodes a polypeptide of the present invention, including those encoding the $^{Ps}$p45 protein of the present invention, or an antigenic fragment thereof, facilitates the production of the large quantities of protein or fragments thereof. The large quantities of the $^{Ps}$p45 protein and/or antigenic fragments thereof produced are useful for making certain vaccines of the present invention.

Accordingly, the present invention provides specific nucleic acid constructs that allow for the expression and isolation of large quantities of the proteins and/or antigens of the present invention, such as the $^{Ps}$p45 protein. These nucleic acids can further contain heterologous nucleotide sequences. To express a recombinant protein of the present invention in a host cell, an expression vector can be constructed comprising the corresponding cDNA. The present invention therefore, provides expression vectors containing nucleic acids encoding the proteins of the present invention, including variants thereof.

Due to the degeneracy of nucleotide coding sequences, other DNA sequences which encode substantially the same amino acid sequence as a nucleic acid encoding a polypeptide of the present invention may be used in the practice of the present invention. These include, but are not limited to, allelic genes, homologous genes from other species, and/or those that are altered by the substitution of different codons that encode the same amino acid residue within the sequence, thus producing a silent change. Host cells comprising the expression vectors of the present invention are also provided. One commonly employed host cell, is an *E. coli* cell.

General methods for the cloning of cDNAs and expression of their corresponding recombinant proteins have been described [see Sambrook and Russell, *Molecular Cloning, A laboratory Manual*, 3$^{rd}$ edition, Cold Spring Harbor Laboratory Press, Cold Spring Harbor L.I. (2000)]. The particular methodology used herein is described in the Examples below. Preferably, all of the nucleic acid constructs of the present invention are sequence confirmed.

In addition, any technique for mutagenesis known in the art can be used to modify the native $^{Ps}$p45 protein of the present invention, including but not limited to, in vitro site-directed mutagenesis [Hutchinson et al., *J. Biol. Chem.*, 253:6551 (1978); Zoller and Smith, *DNA*, 3:479-488 (1984); Oliphant et al., *Gene*, 44:177 (1986); Hutchinson et al., *Proc. Natl. Acad. Sci. U.S.A.*, 83:710 (1986); Wang and Malcolm, *Bio-Techniques* 26:680-682 (1999) the contents of which are hereby incorporated by reference in their entireties]. The use of TAB@ linkers (Pharmacia), etc. and PCR techniques also can be employed for site directed mutagenesis [see Higuchi, "Using PCR to Engineer DNA", in PCR Technology: Principles and Applications for DNA Amplification, H. Erlich, ed., Stockton Press, Chapter 6, pp. 61-70 (1989)].

The present invention also provides nucleic acids that hybridize to nucleic acids comprising the nucleotide sequences of the present invention. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength [see Sambrook and Russell, *Molecular Cloning, A laboratory Manual*, 3$^{rd}$ edition, Cold Spring Harbor Laboratory Press, Cold Spring Harbor L.I. (2000)].

The conditions of temperature and ionic strength determine the "stringency" of the hybridization. For preliminary screening for homologous nucleic acids, low stringency hybridization conditions, corresponding to a $T_m$ of 55° C., can be used, e.g., 5× saline sodium citrate (SSC), 0.1% sodium dodecyl sulfate (SDS), 0.25% milk, and no formamide, or 30% formamide, 5×SSC, 0.5% SDS. Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived strength [see Sambrook and Russell, *Molecular Cloning, A laboratory Manual*, 3$^{rd}$ edition, Cold Spring Harbor Laboratory Press, Cold Spring Harbor L.I. (2000)]. For hybridization with shorter nucleic acids, i.e., oligonucleotides, the position of mismatches becomes more important, and the length of the oligonucleotide determines its specificity.

Preferably a minimum length for a hybridizable nucleic acid is at least about 12 nucleotides; more preferably at least about 18 nucleotides; even more preferably the length is at least about 24 nucleotides; and most preferably at least about 36 nucleotides. In a specific embodiment, the term "standard hybridization conditions" refers to a $T_m$ of 55° C., and utilizes conditions as set forth above. Under more stringent conditions, the $T_m$ is 60° C., and under even more stringent conditions, the $T_m$ is 65° C. for both hybridization and wash conditions respectively.

Polypeptides of the Present Invention

The present invention provides isolated and/or recombinant *Piscirickettsia salmonis* polypeptides, including all of the antigens of the present invention, e.g., the $^{Ps}$p45 protein (plus or minus the amino-terminal signal peptide), *Piscirickettsia salmonis* strain variants thereof, antigenic fragments thereof, and chimeric proteins thereof. In addition, polypeptides containing altered sequences in which functionally equivalent amino acid residues are substituted for those within the wild type amino acid sequence resulting in a conservative amino acid substitution, are also provided by the present invention.

For example, one or more of these amino acid residues within the sequence can be substituted by another amino acid of a similar polarity, which acts as a functional equivalent, resulting in a silent alteration. Substitutes for an amino acid within the sequence may be selected from other members of the class to which the amino acid belongs.

For example, the nonpolar amino acids include alanine, leucine, isoleucine, valine, proline, phenylalanine, tryptophan and methionine. The polar neutral amino adds include glycine, serine, threonine, cysteine, tyrosine, asparagine, and glutamine. The positively charged (basic) amino acids include arginine and lysine. The negatively charged (acidic) amino acids include aspartic acid and glutamic acid.

Particularly preferred conserved amino acid exchanges are:

(a) Lys for Arg or vice versa such that a positive charge may be maintained;
(b) Glu for Asp or vice versa such that a negative charge may be maintained;
(c) Ser for Thr or vice versa such that a free —OH can be maintained;
(d) Gln for Asn or vice versa such that a free $NH_2$ can be maintained; and
(e) Ile for Leu or for Val or vice versa as roughly equivalent hydrophobic amino acids.

All of the polypeptides of the present invention, including antigenic fragments, also can be part of a chimeric protein. In a specific embodiment, a chimeric polypeptide is expressed in a prokaryotic cell. Such a chimeric protein can be a fusion protein used to isolate a polypeptide of the present invention, through the use of an affinity column that is specific for a protein fused to the $^{Ps}$p45 protein, for example. Examples of such fusion proteins include: a glutathione-S-transferase (GST) fusion protein, a maltose-binding protein (MBP) fusion protein, a FLAG-tagged fusion protein, or a poly-histidine-tagged fusion protein. Specific linker sequences such as a Ser-Gly linker can also be part of such a fusion protein.

Indeed, the expression of a chimeric polypeptide, such as the $^{Ps}$p45 protein or fragment thereof, as a fusion protein can facilitate stable expression, and/or allow for purification based on the properties of the fusion partner. Thus the purification of the recombinant polypeptides of the present invention can be simplified through the use of fusion proteins having affinity Tags. For example, GST binds glutathione conjugated to a solid support matrix, MBP binds to a maltose matrix, and poly-histidine chelates to a Ni-chelation support matrix [see Hochuli et al., *Biotechnology* 6:1321-1325 (1998)].

The fusion protein can be eluted from the specific matrix with appropriate buffers, or by treating with a protease that is specific for a cleavage site that has been genetically engineered in between the $^{Ps}$p45 protein, for example, and its fusion partner. Alternatively, a $^{Ps}$p45 protein can be combined with a marker protein such as green fluorescent protein [Waldo et al., *Nature Biotech*. 17:691-695 (1999); U.S. Pat. No. 5,625,048 and WO 97/26333, the contents of which are hereby incorporated by reference in their entireties].

Alternatively or in addition, other column chromatography steps (e.g., gel filtration, ion exchange, affinity chromatography etc.) can be used to purify the recombinant polypeptides of the present invention (see below). In many cases, such column chromatography steps employ high performance liquid chromatography or analogous methods in place of the more classical gravity-based procedures.

In addition, the polypeptides of the present invention, including the $^{Ps}$p45 protein and antigenic fragments thereof can be chemically synthesized [see e.g., Synthetic Peptides: *A User's Guide*, W.H. Freeman & Co., New York, N.Y., pp. 382, Grant, ed. (1992)].

General Polypeptide Purification Procedures

Generally, initial steps for purifying a polypeptide of the present invention can include salting in or salting out, in ammonium sulfate fractionations; solvent exclusion fractionations, e.g., an ethanol precipitation; detergent extractions to free membrane bound polypeptides, such as the $^{Ps}$p45 protein, using such detergents as TRITON X-100, TWEEN-20 etc.; or high salt extractions. Solubilization of membrane proteins, may also be achieved using aprotic solvents such as dimethyl sulfoxide and hexamethylphosphoramide. In addition, high speed ultracentrifugation may be used either alone or in conjunction with other extraction techniques.

Generally good secondary isolation or purification steps include solid phase absorption using calcium phosphate gel, hydroxyapatite, or solid phase binding. Solid phase binding may be performed through ionic bonding, with either an anion exchanger, such as diethylaminoethyl (DEAE), or diethyl [2-hydroxypropyl]aminoethyl (QAE) SEPHADEX or cellulose; or with a cation exchanger such as carboxymethyl (CM) or sulfopropyl (SP) SEPHADEX or cellulose. Alternative means of solid phase binding includes the exploitation of hydrophobic interactions e.g., the use of a solid support such as phenylSepharose and a high salt buffer; affinity-binding immuno-binding, using e.g., a $^{Ps}$p45 protein-antibody bound to an activated support. Other solid phase supports include those that contain specific dyes or lectins etc.

A further solid phase support technique that is often used at the end of the purification procedure relies on size exclusion, such as SEPHADEX and SEPHAROSE gels. Alternatively, a pressurized or centrifugal membrane technique, using size exclusion membrane filters may be employed. Oftentimes, these two methodologies are used in tandem.

Solid phase support separations are generally performed batch-wise with low-speed centrifugation, or by column chromatography. High performance liquid chromatography (HPLC), including such related techniques as FPLC, is presently the most common means of performing liquid chromatography. Size exclusion techniques may also be accomplished with the aid of low speed centrifugation. In addition size permeation techniques such as gel electrophoretic techniques may be employed. These techniques are generally performed in tubes, slabs or by capillary electrophoresis.

Almost all steps involving polypeptide purification employ a buffered solution. Unless otherwise specified, generally 25-100 mM concentrations of buffer salts are used. Low concentration buffers generally imply 5-25 mM concentrations. High concentration buffers generally imply concentrations of the buffering agent of between 0.1-2.0 M concentrations. Typical buffers can be purchased from most biochemical catalogues and include the classical buffers such as Tris, pyrophosphate, monophosphate and diphosphate and the Good buffers such as Mes, Hepes, Mops, Tridine and Ches [Good et al., *Biochemistry*, 5:467 (1966); Good and Izawa, *Meth. Enzymol.*, 24B:53 (1972); and Fergunson and Good, *Anal. Biochem.*, 104:300 (1980].

Materials to perform all of these techniques are available from a variety of commercial sources such as Sigma Chemical Company in St. Louis, Mo.

Antibodies to the Polypeptides of the Present Invention

The polypeptides of the present invention, and antigenic fragments thereof, as produced by a recombinant source, or through chemical synthesis, or as isolated from natural sources; and variants, derivatives or analogs thereof, including fusion proteins, may be used as an immunogen to generate antibodies. Such antibodies include but are not limited to polyclonal, monoclonal, chimeric including single chain, Fab fragments, and a Fab expression library. Such antibodies can be used in diagnostic kits or as components in vaccines.

Specific anti-$^{Ps}$p45 protein antibodies of the invention, for example, may be cross-reactive, that is, they may recognize a $^{Ps}$p45 protein or closely related protein derived from a different source (e.g., a *Piscirickettsia*-like bacterium). Polyclonal antibodies have greater likelihood of cross-reactivity. Alternatively, an antibody of the invention may be specific for a single form of a $^{Ps}$p45 protein for example, such as a specific fragment of the $^{Ps}$p45 protein that has the amino acid sequence of SEQ ID NO:2 or closely related variant thereof.

In a particular aspect of the present invention compositions and uses of antibodies that are immunoreactive with the $^{Ps}$p45 protein are provided. Such antibodies "bind specifically" to the $^{Ps}$p45 protein, meaning that they bind via antigen-binding sites of the antibody as compared to non-specific binding interactions. The terms "antibody" and "antibodies" are used herein in their broadest sense, and include, without limitation, intact monoclonal and polyclonal antibodies as well as fragments such as Fv, Fab, and F(ab') fragments, single-chain antibodies such as scFv, and various chain combinations. The antibodies may be prepared using a variety of well-known methods including, without limitation, immunization of animals having native or transgenic immune repertoires, phage display, hybridoma and recombinant cell culture.

Both polyclonal and monoclonal antibodies may be prepared by conventional techniques. [See, for example, *Monoclonal Antibodies, Hybridomas: A New Dimension in Biological Analyses*, Kennet et al. (eds.), Plenum Press, New York 37 (1980); and Antibodies: A Laboratory Manual, Harlow and Land (eds.), Cold Spring Harbor Laboratory Press, Cold Spring Harbor, N.Y., (1988)].

Various procedures known in the art may be used for the production of polyclonal antibodies to the $^{Ps}$p45 protein, variants or derivatives or analogs thereof. For the production of an antibody, various host animals can be immunized by injection with the $^{Ps}$p45 protein, variant or a derivative (e.g., or fusion protein) thereof or fragment thereof, including but not limited to rabbits, mice, rats, sheep, goats, etc. In one embodiment, the $^{Ps}$p45 protein can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, and dinitrophenol.

For preparation of monoclonal antibodies directed toward the $^{Ps}$p45 protein, variant, or analog, or derivative thereof, any technique that provides for the production of antibody molecules by continuous cell lines in culture may be used. These include but are not limited to the hybridoma technique originally developed by Kohler and Milstein [*Nature*, 256:495-497 (1975)], as well as the trioma technique, and the human B cell hybridoma technique [Kozbor et al., *Immunology Today*, 4:72 (1983); Cote et al., *Proc. Natl. Acad Sci. U.S.A.*, 80:2026-2030 (1983)].

The monoclonal antibodies of the present invention include chimeric antibodies versions of antibodies originally produced in mice or other non-human animals. Techniques developed for the production of "chimeric antibodies" by splicing the genes from a mouse antibody molecule specific for a $^{Ps}$p45 protein for example, together with genes from a fish antibody of appropriate biological activity (e.g., a salmon) can be used. Such chimeric antibodies are within the scope of this invention [see in general, Morrison et al., *J Bacteriol*, 159:870 (1984); Neuberger et al., *Nature*, 312:604-608 (1984); Takeda et al., *Nature*, 314:452-454 (1985)].

Hybridoma cell lines that produce monoclonal antibodies specific for the polypeptides of the present invention are also provided by the present invention. Such hybridomas may be produced and identified by conventional techniques.

One method for producing such a hybridoma cell line comprises immunizing an animal with a polypeptide, harvesting spleen cells from the immunized animal, fusing the spleen cells to a myeloma cell line, thereby generating hybridoma cells, and identifying a hybridoma cell line that produces a monoclonal antibody that binds the polypeptide. The monoclonal antibodies produced by hybridomas may be recovered by conventional techniques.

According to the invention, techniques described for the production of single chain antibodies [U.S. Pat. Nos. 5,476,786, 5,132,405, and 4,946,778, the contents of which are hereby incorporated by reference in their entireties] can be adapted to produce e.g., $^{Ps}$p45 protein-specific single chain antibodies. An additional embodiment of the invention utilizes the techniques described for the construction of Fab expression libraries [Huse et al., *Science*, 246:1275-1281 (1989)] to allow rapid and easy identification of monoclonal Fab fragments with the desired specificity for a $^{Ps}$p45 protein, variant, derivatives, or analogs.

Antibody fragments which contain the idiotype of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent.

In the production of antibodies, screening for the desired antibody can be accomplished by such techniques as radioimmunoassay, enzyme-linked immunosorbant assay (ELISA), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays.

In one embodiment, antibody binding is detected by detecting a label, e.g., a fluorescent label such as fluorescene isothiocyanate (FITC), on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of the $^{Ps}$p45 protein, one may assay generated hybridomas for a product which binds to the $^{Ps}$p45 protein fragment containing such an epitope and choose those which do not cross-react with modified $^{Ps}$p45 proteins that do not contain that epitope. For selection of an antibody specific to a $^{Ps}$p45 protein from a particular source, one can select on the basis of positive binding with $^{Ps}$p45 protein expressed by or isolated from that specific source.

SRS Vaccines

The present invention provides SRS vaccines. One particular embodiment is a non-mineral oil injection prime vaccine comprising one or more antigens from *Piscirickettsia salmonis*, as disclosed below. In a preferred embodiment of this type, inactivated recombinant bacteria (bacterins) comprise the *Piscirickettsia salmonis* antigens.

The present invention also provides SRS vaccines that also are designed to protect against one or more other fish pathogens. For example, furunculosis is an infectious ulcerative disease of salmon and trout caused by the bacterium *Aeromonas salmonicida.*

Other fish pathogens include but are not limited to:

| PATHOGEN (antigen) | RELATED DISEASE |
|---|---|
| IPN virus | Infectious pancreatic necrosis |
| *Vibrio anguillarum* | Vibrosis |
| *Vibrio salmonicida* | Cold water Vibriosis (Hitra disease) |
| *Moritella viscosus* | Winter sores disease |
| *Photobacterium damsela* (subspecies *Piscicida*) | Pasteurellosis |
| *Lactococcus garviae* | Streptococcosis |
| *Streptococcus iniae* | |
| *Moritella viscosus* | Winter Sores |
| *Noccardia kampachi* | |
| *Renibacterium salmoninarum* | |
| ISA Virus | Infectious *Salmon Anemia* |
| IHN Virus | Infectious Heamorhagic Necrosis |
| SPD Virus | Salmon pancreatic disease |
| SD Virus | Sleeping disease |

The vaccines for these various diseases can be prepared from whole cells, bacterins, killed and/or attenuated virus, protein extracts, recombinant DNA vaccine vectors, isolated antigens, recombinant antigens and mixtures thereof. Under particular circumstances, as for *Photobacterium damsela* and *Aeromonas salmonicida*, the vaccines are preferably prepared from two separate cultures grown under iron-depleted conditions and iron-supplemented conditions, respectively.

In a particular embodiment, a vaccine comprises one or more antigens from *Piscirickettsia salmonis* along with one or more IPN proteins. In still another embodiment, the vaccine comprises one or more antigens from *Piscirickettsia salmonis*, one or more IPN proteins, and one or more antigens to control *Aeromonas salmonicida*. In a particular embodiment of this type, *Aeromonas salmonicida* antigens are two types of whole bacteria grown on bacterial growth media and killed by the addition of formalin.

For an SRS vaccine, *Yersinia ruckeri* was selected as the best candidate, for hosting the antigens of the present invention. One particular Chilean field isolate, a type I *Yersinia ruckeri* strain, was used in the Examples below. Better yields are expected with *Yersinia ruckeri* grown at 20-25° C.

Two IPN viral antigens are exemplified below (see also WO 02/38770, the contents of which are hereby incorporated in its entireties). One of which is derived from Vp2, which is the major outer capsid protein and the other from Vp3, which is an internal protein of the IPN virus. The molecular weight of the Vp2 protein is 52 kDa whereas that of the Vp3 protein is 30 kDa. The IPN proteins of the vaccines of the present invention are preferably purified recombinant proteins. In the Examples below, the IPN proteins are expressed and excreted by transformed yeast (*Pichia pastoris*) and then purified from these yeast cells.

Antigens for a vaccine that also protects against furunculosis can be obtained from whole formalin-killed bacteria *Aeromonas salmonicida*. Early *A. salmonicida* vaccines contain whole *A. salmonicida* bacteria grown in normal growth medium and then inactivated by the addition of formalin. These bacterins contain a mixture of antigens including the surface A-layer, inactivated proteases and lipopoly-saccharide. On the other hand when *A. salmonicida* are grown in normal medium in the total absence of iron, a group of new antigens are expressed. These new antigens are termed iron-regulated outer membrane proteins (IROMPs). IROMPS are highly immunogenic and they provide enhanced protection relative to vaccines containing inactivated *A. salmonicida* grown in normal medium. Four IROMP proteins of having molecular weights of 82 kDa, 77 kDa, 72 kDa and 70 kDa respectively have been identified.

The primary and secondary antibody responses to IROMP antigens in Atlantic salmon (*Salmo salar*) immunized with A+ (iron plus) and A− (iron minus) *Aeromonas salmonicida* bacterins have been reported [O'Dowd et al., *Fish & Shellfish Immunology* 9:125-138 (1999)]. Thus particular vaccines of the present invention contain one strain of *A. salmonicida* (MT004) grown under conditions of iron-limitation and one strain of *A. salmonicida* (MT423) grown under condition of iron-supplementation.

The *Vibro anguillarum* (serotype 01) and *V. anguillarum* (serotype 02) are different serotypes that are not cross-protective and therefore, for broad spectrum protection both antigens are preferably included in the vaccine.

Administration:

The vaccines of the present invention may be administered to fish by any of a number of means including by injection (e.g., intramucuscularly, or intraperitoneally), immersion, and/or through a delivery system for oral vaccination. Vaccinating fish by injection can be performed either with an adjuvant to increase the activity of the antigens, or without an adjuvant. Adjuvants include aqueous adjuvants, such as Alhydrogel or aluminum hydroxide, and oil adjuvants.

Mineral oil adjuvants are commonly employed in fish vaccines and are included in the present invention. One such adjuvant is mannide oleate in a mineral oil solution. In a particular embodiment of this type, the vaccine comprises 70% mannide oleate in a mineral oil solution. Another mineral oil adjuvant of the present invention consists of white mineral oil, Span 80 [sorbitan monooleate], and Tween 80 [polyoxyethylene sorbitan monooleate]. In a particular embodiment, a vaccine comprises 80% of an adjuvant having the following formulation: 944 ml white mineral oil: 50.3 ml Span 80: 5.7 ml Tween 80.

Since mineral oil adjuvants generally cause damage to the fish at the site of injection (lesions, which have to be removed before sale) and they depress growth rates for a period of time, the present invention also provides non-mineral oil adjuvants. Synthetic non-mineral oil adjuvants include those commercially available from Seppic SA. Montamide, e.g., Montamide ISA563, Montamide ISA 575, and Montamide ISA 711. Montamide ISA 711, exemplified below, is essentially mannide oleate in an oil solution. Particular embodiments of a vaccine of the present invention comprise 50% of either Montamide ISA563 or Montamide ISA 575, or 70% Montamide ISA 711.

Alternatively, vaccines can be applied by a long-term immersion bath. In one such embodiment, vaccination via an immersion bath is preceded by hyperosmotic treatment [see Huising et al., *Vaccine* 21:4178-4193 (2003)]. In another embodiment, a vaccine is administered by spraying the fish.

The present invention also includes orally-delivered vaccines. Generally, oral vaccines are prepared by either top-dressing the food with an antigen (e.g., by spray drying) or by incorporating the antigen in the food [see, e.g., Vinitnantharat et al., *Adv. Vet. Med.* 41:539-550 (1999)]. Other techniques include water-in-oil methods, bioencapsulation, microencapsulation incorporation into liposomes, incorporation in hollow feed prills, and incorporation into microparticle carriers, e.g., poly-lactide co-glycolide carrier particles [see, e.g., Singh et al., *Expert Opin. Biol. Ther.* 4(4):483-491 (2004)]. Yet another method entails expressing the antigen in algae.

Booster vaccines are also part of the present invention. In a particular embodiment, an oily emulsion oral booster vaccine comprising one or more antigens from *Piscirickettsia salmonis* is used after the primary vaccination. Preferably the oily emulsion is made up of water:oil in the range of 6:4 to 4:6. The level of free fatty acids should not be greater than 5% by weight of the oil and preferably no greater than 3%. Particular oils include whole fish body oil and neutral marine oil. The emulsifier is preferably food grade. Lecithin can be used as such an emulsifier, e.g., soya lecithin.

The emulsifier generally comprises from approximately 0.1% to approximately 5% by weight of the total emulsion. In a particular embodiment of this type, the oily phase of the emulsion is 47% v/v refined fish body oil plus 3% v/v lecithin (Bolec MT) which are mixed, sterilized with gamma irradiation and then blended, using an homogenizer. The aqueous antigen phase can be diluted with phosphate buffered saline [see, GB 2 255 909, PCT/GB9101828, WO/92106599, the contents of which are hereby incorporated by reference in their entireties].

Injection vaccination is usually conducted on a commercial scale using a fixed dose automatic repeating syringe or an automatic injection vaccination machine. These methods are designed to deliver a fixed dose of usually 0.1 or 0.2 ml per fish. The vaccine is injected through the body wall into the intra-peritoneal cavity. It is also possible to immunise fish by injecting the vaccine into the dorsal sinus. Generally, fish are vaccinated by injection following anesthetization.

Immersion vaccination can be performed as follows:

Dilute 1 liter of vaccine with 9 liters of clean hatchery water. Then Drain and weigh a netful of fish and dip fish in the diluted vaccine for 30 to 60 seconds ensuring that fish are totally immersed in the vaccine. After 30 to 60 seconds lift net, drain and return fish to holding tank. Repeat until 100 kg of fish have been dipped into 10 liters of diluted vaccine.

Oral vaccination can be performed as follows:

A container of vaccine is brought to room temperature (20° C.) and then shaken prior to use. The vaccine is mixed with the fish feed so that the vaccine is coated onto the surface of the fish feed and adsorbed. The total vaccine dose should be fed over a 10 day period at 1/10 dose per fish per day.

Recombinant Enteric Bacterial Vaccines

The present invention further provides methods that employ recombinant enteric bacteria not present in humans to express foreign recombinant bacterial surface antigens. Heretofore, these bacterial surface antigens were extremely difficult to express, particularly in a vector for use in a vaccine. Preferably, this aspect of the invention pertains to recombinant enteric bacteria that encode a foreign surface antigen from an intracellular pathogen of fish. The enteric bacterium is also preferably one that infects fish.

As exemplified herein, *Yersinia ruckeri*, a non-human enteric bacterium, can be used as a recombinant vector. Examples of other appropriate enteric bacteria include *Vibrio anguillarum, Vibrio salmonicida, Moritella viscosus*, and *Photobacterium damsela*. Preferably, the recombinant bacterium is inactivated (i.e., a bacterin).

Any surface antigen from an intracellular pathogen can be used as the foreign surface antigen. IROMPS, discussed below, are examples of appropriate surface antigens. For example, a nucleic acid encoding a surface antigen from one fish enteric bacterium can be inserted into another fish enteric bacterium to generate such a recombinant enteric bacterium. In a particular embodiment, a nucleic acid encoding a secreted protein, such as a protease, is used in place of a nucleic acid encoding a surface antigen in the recombinant enteric bacterial vector.

Methods of making these recombinant enteric bacteria, methods for their inactivation, methods for the preparation of vaccines containing these recombinant enteric bacteria, and methods of administering the vaccines are the same as provided for the recombinant *Yersinia ruckeri* vaccines exemplified herein. Appropriate vaccination recipients are provided in the section that follows below.

Vaccination Recipients

Salmonid rickettsial septicemia (SRS) was first observed in salmonids, which are the fish in the Salmonidae family, of the order Salmoniformes and of the class Osteichthyes. Salmonids are elongate bony fish with the last three vertebrae upturned, having a small adipose fin without fin rays between the dorsal fin and the tail. Many species of salmonids live in the sea, but enter fresh water to spawn. The Salmonidae family includes salmon, trout, char, and whitefish (see Table 1, below, which provides a non-exhaustive list of fish in the Salmonidae family).

TABLE 1

| *Salmonidae* Family | |
|---|---|
| *Coregonus clupeaformis* | Lake whitefish |
| *Coregonus hoyi* | Bloater |
| *Oncorhynchus keta* | Chum salmon |
| *Oncorhynchus gorbuscha* | Pink salmon |
| *Oncorhynchus kisutch* | Coho salmon (silver salmon) |
| *Oncorhynchus masou* | cherry salmon (masou salmon) |
| *Oncorhynchus nerka* | Sockeye salmon |
| *Oncorhynchus tshawytscha* | King salmon (chinook salmon) |
| *Prosopium cylindraceum* | Round whitefish |
| *Oncorhynchus clarki* | Cutthroat trout |
| *Oncorhynchus mykiss* | Rainbow trout |

TABLE 1-continued

Salmonidae Family

| | |
|---|---|
| Salmo salar | Atlantic salmon |
| Salmo trutta | Brown trout |
| Salmo trutta X S. fontinalis | Tiger hybrid-trout |
| Salvelinus alpinus | Arctic charr |
| Salvelinus confluentus | Bull trout |
| Salvelinus fontinalis | Brook trout |
| Salvelinus leucomaenis | Japanese charr (white spotted charr) |
| Salvelinus malma | Dolly varden (Miyabe charr) |
| Salvelinus namaycush | Lake trout |
| Thymallus thymallus | Grayling |

Reports of (SRS) and closely related Rickettsial syndrome afflicting fish as disparate as tilapia, white sea bass, rainbow trout, steelhead trout, grouper, Chilean sea bass, tiger puffers, red sea bream, blue-eyed plecostomus, striped bass, fluke, Atlantic cod, butter fish, ocean pout, spotted hake, summer and winter flounder, weakfish, yellowtail flounder, Windowpane flounder (*Scophthalmus aquosus*) cultured amberjack. three lined grunt, and blue eyed plecostomus indicates that the vaccines of the present invention may be used to vaccinate essentially any fish. Preferably the fish are in the *Teleosti* grouping of fish, i.e., teleosts. Both the Salmoniformes order (which includes the Salmonidae family) and the Perciformes order (which includes the Centrarchidae family) are contained within the *Teleosti* grouping.

Aside from the Salmonidae family and those included above, examples of potential vaccination recipients include the Serranidae family, the Sparidae family, the Circhlidae family, the Centrarchidae family, the three-Line Grunt (*Parapristipoma trilineatum*), and the Blue-Eyed Plecostomus (*Plecostomus* spp).

Some Members of the Serranidae Family

| TAXON NAME | COMMON NAME |
|---|---|
| Centropristis ocyurus | Bank sea bass |
| Centropristis philadelphicus | Rock sea bass |
| Centropristis striata | Black sea bass |
| Diplectrum bivittatum | Dwarf sandperch |
| Diplectrum formosum | Sand perch |
| Epinephelus flavolimbatus | Yellowedge grouper |
| Epinephelus morio | Red grouper |
| Serranus phoebe | Tattler |
| Serranus tortugarum | Chalk bass |

Some Members of the Sparidae family

| TAXON NAME | COMMON NAME |
|---|---|
| Archosargus probatocephalus | Sheepshead |
| Archosargus rhomboidalis | Sea bream |
| Calamus penna | Sheepshead porgy |
| Lagodon rhomboides | Pinfish |
| Pagrus Major | Red Sea bream |
| Sparus aurata | Gilthead Sea bream |
| Stenotomus chrysops | Scup |

Some Members of the Cichlidae family

| TAXON NAME | COMMON NAME |
|---|---|
| Aequidens latifrons | Blue acara |
| Cichlisoma nigrofasciatum | Congo cichlid |
| Crenichichla sp. | Pike cichlid |
| Pterophyllum scalare | Angel fish |
| Tilapia mossambica | Mozambique mouth breeder |
| Oreochromis spp | Tilapia |
| Sarotherodon aurea | Golden Tilapia |

Some Members of the Centrarchidae family

| TAXON NAME | COMMON NAME |
|---|---|
| Ambloplites rupestris | Rock bass |
| Centrarchus macropterus | Flier |
| Elassoma evergladei | Everglades pigmy sunfish |
| Elassoma okefenokee | Okefenokee pigmy sunfish |
| Elassoma zonatum | Banded pigmy sunfish |
| Enneacanthus gloriosus | Bluespotted sunfish |
| Enneacanthus obesus | Banded sunfish |
| Lepomis auritus | Redbreast sunfish |
| Lepomis cyanellus | Green sunfish |
| Lepomis cyanellus X L. gibbosus | Green x pumpkinseed |
| Lepomis gibbosus | Pumpkinseed |
| Lepomis gulosus | Warmouth |
| Lepomis humilis | Orange-spotted sunfish |
| Lepomis macrochirus | Bluegill |
| Lepomis megalotis | Longear sunfish |
| Micropterus coosae | Shoal bass |
| Micropterus dolomieui | Smallmouth bass |
| Micropterus punctulatus | Spotted bass |
| Micropterus salmoides | Largemouth bass |
| Pomoxis annularis | White crappie |
| Pomoxis nigromaculatus | Black crappie |

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLES

Example 1

Identification of Antigens in *Piscirickettsia salmonis*

Summary

High titer anti-*Piscirickettsia salmonis* (Ps) serum was obtained from rabbits for the screening for the expression of Ps antigens. High molecular weight DNA was extracted from Ps cells to be cloned in *E. coli*. A cDNA library was constructed in phage (λGEM-12-PROMEGA) following a strategy detailed below.

The cDNA library was transferred to plasmid vectors to allow the screening of bacteria colonies using rabbit antiserum. Several successive screenings were performed on more than 30,000 colonies. Two potential antigens were identified with Western blots, one of which is the $^{Ps}$p45 protein.

DNA inserts of the clones producing the $^{Ps}$p45 protein were analysed and the complete nucleotide sequence of the clone was obtained [SEQ ID NO: 1]. The coding sequence of the $^{Ps}$p45 protein was reproduced by PCR and then introduced into the expression vector pARHS2. High yield expression was obtained in *E. coli*.

To prepare an efficacious vaccine, a Chilean strain of *Yersinia ruckeri* was selected as the host. The pARHS2 expression vector proved to be ineffidient in *Yersinia ruckeri*. The nucleic acid constructs were then transferred into a pSE380 expression vector (e.g., from Invitrogen Life Technologies). Production of the recombinant antigen was not obtained in *Yersinia ruckeri* using this vector. An alternative design was therefore chosen that yielded an efficient expression of the $^{Ps}$p45 protein in *Yersinia ruckeri* using the original cloning vector. The same design also permitted the expression of other *Piscirickettsia salmonis* antigens in *Yersinia ruckeri*.

Serums

*Piscirickettsia salmonis* cells obtained from Puerto Montt, Chile were inactivated with about 70% ethanol and/or with about 0.5% formaldehyde. The inactivated cells were dialyzed overnight against bicarbonate buffer and then lyophilized. Three rabbits were immunized with four monthly subcutaneous injections of 300 µg of the lyophilized cells over the course of four months, with each rabbit receiving a total of four injections. The resulting rabbit antiserum identified numerous Ps antigens via Western blot. The $^{Ps}$p45 protein was identified in this manner. A recombinant $^{Ps}$p45 protein was then produced in *E. coli* and used to immunize mice. The rabbit antiserum also recognised this recombinant Ps antigen.

Clones and Sequencing

Expression libraries: An expression library containing Ps cDNAs was constructed using phage [λGEM-12-PROMEGA]. Based on the number of clones and the size of inserts, it appeared to be a high quality phage library. However, screening the phage library directly could identify no positive clones. The yield of recombinant antigens may have been too low to during the phage infection to allow the detection. The Ps nucleic acids of the phage library were therefore transferred to plasmid vectors. However, the screening of the resulting plasmid library proved difficult, due to a high background. Serum adsorption on *E. coli* antigens greatly reduced the background and allowed the rapid identification of two antigens. The $^{Ps}$p45 protein was one of the two antigens identified. Subsequent screenings of the approximately 30,000 clones failed to identify any further antigens.

Sequencing: The plasmid that expressed the $^{Ps}$p45 protein contains 17,000 base pairs. A restriction map of the plasmid was prepared and pertinent restriction fragments were subcloned. After several rounds of manipulations, a nucleic acid comprising 2,096 base pairs was isolated that remained capable of expressing the $^{Ps}$p45 protein. The nucleotide sequence of that nucleic acid was then determined (SEQ ID NO: 19) and is provided below. The corresponding amino acid sequence, predicts a secreted protein of 438 amino acids with a 22 residues signal peptide (underlined—italic in the sequence below). The predicted molecular weight of the mature protein after secretion and cleavage of the signal peptide is 44,021 daltons.

The PSORT algorithm was applied to the amino acid sequence to predict the protein localization [Nakai and Kanehisa, *PROTEINS: Structure, Function, and Genetics* 11: 95-110 (1991)]. This algorithm gave the highest score (0.944) for an outer membrane localization and a minor score (0.376) for a periplasmic localization. Localization in the cytoplasmic and inner membrane was ruled out with scores of 0.000. Outer membrane proteins are potential targets for neutralizing antibodies. No homology with other proteins sequenced to date could be found.

```
  1  ...  .CC AAG AAC TAT CAA AAA CTA TAT AGG CAA AGT ATA AAG TCT GAA   44

45  GCT TAA CCT TTG CTT AAA TGT ACA TCA GGC TTA AGG TGA TTT CTG TTG   92

93  AGT ATT TTC AGA GTC TTA AGC TCA ATT TAA TCT TTC TTA AGG TTG AAA  140

141  ACA GGC TAA AAT CAA CAT TTT GAT AAA ATT ATT AAT TTT TTT TTA TTG  188

189  TTC TTT TTT AAT CGG TTT TTA TCC TAA TTT GAT AGA TAG TTA TCG AAA  236

237  TTC AAT AAG TTT TGT TTT TAA TTG AAT TTT TTT TAC GAG TTT GGG TTT  284

285  TAC AAA GTG AAT TTA CCT GGT TAT AGT AGC CCC AGT TGC TTA ATA GCA  332
                                                              Met Lys   2

333  CTT AAA TGT GTA TCC AGA TAA AAA CAA GTT AGG GTA AAA AGA ATA AAA  380
  3  Val Lys Met Ile Val Ala Ala Val Ala Val Ala Gly Leu Thr Ala Thr  18

381  GTA AAA ATG ATT GTE GCA GCT GTA GCT GTT GCA GGT TTA ACA GCG ACT  428
 19  Ala Ala Asn Ala Ala Asp Asn Gly Lys Leu Gln Leu Gln Ile Asn Gln  34

429  GCC GCA AAT GCC GCT GAT AAT GGT AAG CTT CAA TTA CAA ATC AAC CAA  476
 35  Leu Lys Ala Gln His Thr Gln Leu Gln Gln Val Ala Asn Leu Gln      50

477  TTG AAG GCG CAA CAC ACT CAA CTT CAA CAG CAA GTT GCT AAT CTG CAA  524
 51  Gly Gln Gly Gln Thr Thr Gly Ala Val His Val Gly Ala Val Gly Gly  66

525  GGT CAA GGC CAA ACT ACT GGT GCC GTT CAC GTT GGC GCT GTT GGT GGT  572
```

-continued

```
 67 Glu Leu Ile Ser Glu Asn Asn Tyr Asp Gly Arg Gly Leu Asp Leu Leu    82
573 GAA CTA ATC TCT GAA AAT AAC TAC GAT GGT CGT GGC TTA GAT CTT CTT    620

83 Lys Ser Leu Ala Lys Ala Gly Ser Asn Ala Pro Leu Leu Thr Ile Gly    98
621 AAA TCA TTA GCG AAA GCA GGC AGC AAT GCA CCG TTA TTA ACT ATT GGT    668

99 Gly Thr Leu Glu Ala Asp Ala Gln Met Asn Arg Asn Gly Asn Val Gly   114
669 GGT ACG TTA GAA GCT GAT GCG CAA ATG AAC CGT AAC GGT AAT GTT GGA    716

115 Ser Gly Ser Thr Ser Gly Asp Pro Ser Gly Leu Asn Tyr Thr Asp Gly   130
717 TCT GGT TCT ACT TCT GGT GAC CCT TCT GGC CTT AAC TAT ACT GAT GGA    764

131 Thr Ser Ser Ser Ala Phe Tyr Leu Asp Thr Ala Arg Ile Asp Ile Leu   146
765 ACT AGC AGT TCT GCA TTC TAT TTA GAT ACT GCA CGT ATT GAT ATC TTA    812

147 Ala His Val Asn Asp Trp Val Asn Gly Glu Ile Ser Tyr Asp Leu Asn   162
813 GCG CAT GTG AAT GAC TGG GTT AAC GGT GAA ATC TCG TAT GAC TTA AAT    860

163 Gly Asp Ser Gly Leu His Thr Gly Ser Leu Leu Val Gly Asn Leu Asn   178
861 GGT GAT AGT GGT CTT CAC ACT GGT AGC CTT TTA GTG GGT AAC CTC AAT    908

179 Gln Leu Pro Val Tyr Gly Gln Ile Gly Lys Phe Tyr Pro Asp Ala Gly   194
909 CAA TTA CCA GTT TAT GGT CAA ATC GGT AAA TTC TAC CCA GAT GCA GGT    956

195 Leu Phe Glu Leu Ala Ser Asp Asp Val Tyr Ser Ser Ser Leu Val Lys   210
957 TTG TTT GAA TTA GCT AGT GAT GAT GTT TAT TCT TCT AGC TTA GTC AAG   1004

211 Arg Tyr Phe Arg Pro Asp Ala Gln Asn Gly Ala Ser Val Gly Phe Tyr   226
1005 CGT TAT TTC CGT CCA GAT GCG CAA AAT GGT GCA TCT GTA GGC TTC TAT   1052

227 Lys Ala Gly Leu His Thr Ser Leu Thr Ala Phe Lys Thr Ser Ala Pro   242
1053 AAA GCA GGC TTA CAT ACT TCT TTA ACT GCA TTT AAA ACG TCT GCT CCA   1100

243 Gln Ala Asn Ala Ala Asn Tyr Asn Gln Ala Thr Ser Asp Trp Ser Ala   258
1101 CAA GCT AAT GCT GCT AAC TAT AAC CAA GCA ACT AGT GAT TGG TCT GCA   1148

259 Gln Ala Asp Tyr Thr Phe Asn Ala Gly Gln Val Asn Ala Thr Ile Gly   274
1149 CAA GCG GAT TAC ACT TTT AAT GCA GGT CAA GTC AAT GCC ACT ATA GGT   1196

275 Ala Gly Tyr Leu Ser Asn Met Val Asn Thr Asn Asp Ser Phe Thr Ala   290
1197 GCA GGT TAC TTA TCT AAT ATC GTG AAT ACC AAT GAC AGC TTC ACT GCA   1244

291 Thr Gly Ala Gly Thr Gly Thr Gln Lys Asp Arg Leu Pro Met Ala Asn   306
1245 ACA GGT GCA GGA ACT GGT ACA CAA AAA GAT CGG CTA CCG ATG GCT AAT   1292

307 Val Ser Ala Lys Ile Gly Phe Gly Pro Phe Glu Ala Leu Ala Thr Tyr   322
1293 GTA AGC GCT AAG ATT GGC TTT GGT CCA TTT GAA GCC CTT GCT ACT TAT   1340

323 Ala Gln Thr Leu Lys Gly Leu Ala Asn Thr Thr Gly Gly Thr Thr Lys   338
1341 GCT CAA ACA TTA AAA GGT TTG GCG AAT ACT ACA GGT GGT ACA ACG AAG   1388

339 Leu Lys Ala Phe Asp Leu Glu Gly Ala Tyr His Phe Gln Ala Val Lys   354
1389 TTG AAA GCC TTT GAT TTA GAA GGT GCT TAC CAC TTC CAA GCT GTG AAG   1436

355 Pro Met Thr Val Met Leu Gly Tyr Ser Arg Thr Tyr Gly Phe Asp Lys   370
1437 CCG ATG ACT GTG ATG TTA GGT TAT AGC CGT ACA TAT GGC TTT GAT AAG   1484

371 Val Gly Pro Val Asp Gln Phe Ile Asp Gly Asn Thr Ala Ile Thr Ile   386
1485 GTT GGA CCT GTT GAT CAG TTT ATT GAT GGT AAT ACT GCG ATT ACT ATC   1532
```

-continued

```
 387 Asn Asn Lys Lys Asp Gln Trp Leu Leu Gly Val Asn Ser Glu Val Phe  402
1533 AAT AAC AAA AAA GAC CAA TGG TTA TTG GGT GTA AAC TCT GAA GTA TTT 1580

403 Lys Asn Thr Thr Val Gly Leu Glu Tyr Ala Arg Val Gly Gln Leu Asp  418
1581 AAG AAC ACA ACG GTT GTT CTT GAG TAT GCG CGT GTA GGT CAG CTT GAT 1628

419 Ser Thr Gly Thr Asp Thr Asn Arg Tyr Asn Val Leu Thr Ala Asp Met  434
1629 AGC ACA GGT ACT GAC ACT AAC CGC TAC AAC GTA TTG ACT GCG GAT ATG 1676

435 Thr Val Lys Phe ***
1677 ACT GTT AAG TTC TAA TTT AAG AAC TTT AAA GTT TTC AAA AAG GCG CTG 1724

1725 CGG CGC CTT TTT TTA TGG GCG TTA ATT ATT GGT AAT GTA GGC TAG TAT 1772

1771 TTA AAT TTG TGA GTG ATG AGA GAT GAA AAA TTT AAT CTA TGC ACA GCG 1820

1821 TTT GCT TTA TTT TGC CGT ATT GAT TGC GGT GAT TGT CAC CTT TGT TCA 1868

1869 GCC ATT TCT AAT GCC GAT TAA GCT TGC TGA TGT GCC TTT AAT GCC GCT 1916

1917 CGT GGT CGC TTC GAT TTA TTC CTT GAT TTT TGC TGC AGC TTT AGC ATT 1964

1965 AGC TGC ATA TAA ATT ACC GAG CAA AGC TGG TTG GCC GCG GTT TTT GTT 2012

2013 GGT GAT TTT ATT TAT TGG GGA TGC GAT GCC TGC GGT AAA AAA CTG GCT 2060

2061 AGT GCT TTG GCA TAC GAC GGA GCT TTT TGC GA
```

Expression

Expression of the $^{Ps}$p45 protein antigen in *E. coli*: Two constructs were made for expression of the recombinant $^{Ps}$p45 protein. The expression system chosen is the standard T7-BL21 system [commercially available from Gene Therapy System Inc.] The system relies on a two tier amplification of induction of production. The first tier is the synthesis of the very powerful T7 phage RNA polymerase by induction with IPTG of a lac promoter. This polymerase binds a specific T7 sequence and actively transcribes RNA. The second tier relies on the placement of this T7 sequence just upstream of the gene of interest on the high copy plasmid pARHS.

Two constructs were prepared. Construct A contained the entire coding sequence for the $^{Ps}$p45 protein (having the nucleotide sequence of SEQ ID NO:1). The protein expressed might be secreted or expressed at the surface of the *E. coli* host cell. Construct B encodes a $^{Ps}$p45 protein (having the nucleotide sequence of SEQ ID NO: 3) that only lacks the coding region for the signal peptide. Without the signal peptide, the $^{Ps}$p45 protein can't be secreted. The expression of the $^{Ps}$p45 protein (having the amino acid sequence of SEQ ID NO: 4) would be expected to lead to a higher protein yield and a lesser cell toxicity than the expression of full-length $^{Ps}$p45 protein (having the amino acid sequence of SEQ ID NO: 2).

Both constructs were grown on a small scale (100 ml). The expression of the $^{Ps}$p45 protein was designed to require IPTG induction. However, high levels of induction of the recombinant $^{Ps}$p45 protein were found in both the preculture and the non-induced culture. This type of result is not uncommon when the cascade T7 promoter is used. Apparently, the $^{Ps}$p45 protein is easily produced in *E. coli*, which is, unfortunately, highly detrimental to the stability of the strain.

The $^{Ps}$p45 protein lacking the signal peptide accumulated in the cytoplasm of the bacteria, amounting to approximately 10-20% total protein (estimated from Coomassie blue stained SDS-PAGE). The full-length protein accumulated too, and a fraction was shown to be exported in the culture medium. This is a reasonable result since *E. coli* is not a good secretor. Moreover the strain was grown at 37° C., a temperature that might not be optimal for a protein originating from a psychro- or mesophillic organism.

Expression of the $^{Ps}$p45 protein in Chilean strains of *Yersinia ruckeri* (Yr): The T7 promoter based expression system only works in *E. coli* strains is that comprise the lysogenic phage DE3, which encodes T7 polymerase. Since *Yersinia ruckeri* does not encode T7 polymerase, constructs encoding the full-length ${}^{Ps}$p45 protein and the ${}^{Ps}$p45 protein lacking the signal peptide were transferred into a new vector having a promoter derived from the lactose operon. Although *Yersinia ruckeri* is lactose negative, the lac promoter can be induced by the lactose analogue IPTG. *Yersinia ruckeri* strain 224 serotype I was selected, which lacks any antibiotic resistance.

Two expression plasmids were constructed that were derived from plasmid pSE380 obtained from Invitrogen (USA). The characteristics of the plasmid are the followings:

1. ColE1 origin of replication to maintain the plasmid in various Gram negative hosts.
2. Ampicillin resistance for the selection of the bacteria that contain the plasmid. This antibiotic is not generally used in aquaculture.
3. $Iacl^{q}$ is a superproducer of Iacl, the activator protein of lac promoters or promoters such as Ptrc that uses the lad activator binding sequence. In the presence of lactose or its stable (not metabolised) analogue iso-propyl-thiogalactoside (IPTG) lad turns the Ptrc promoter on.
4. Ptrc promoter a synthetic promoter containing Iacl activator binding sequence.
5. RBS, ribosome binding site optimised for *E. coli*, it is also active in *Yersinia ruckeri.*
6. ATG is the initiator codon of the recombinant protein, it is placed at optimum distance from the RBS for efficient translation of the mRNA into protein. The ATG is included in the Nco I restriction site.

7. The super linker provides a large panel of restriction sites for easy insertion of recombinant genes.

8. Term is a RNA transcription terminator, it prevents the transcription complex to go too far into the plasmid and jeopardise the stability of the plasmid.

A recombinant nucleic acid encoding the $^{Ps}$p45 protein was produced by PCR in order to introduce a Nco I site on the initiator codon and a Bam HI site after the stop signal. The recombinant nucleic acid was introduced between the Nco I and the Bam HI site of the superlinker. A second recombinant nucleic acid encoding the $^{Ps}$p45 protein was produced by PCR, an Nco I site was introduced in the correct reading frame after the putative signal peptide. Similarly, a Bam HI site was added after the stop signal. The recombinant nucleic acid was introduced between the Nco I and the Bam HI site of the superlinker. Both plasmids were introduced into *E. coli* for amplification, extracted and introduced by electroporation into *Yersinia ruckeri* strain 224. Upon culture and induction, no recombinant $^{Ps}$p45 protein could be detected.

An alternative strategy had to be designed. Unfortunately, little was known about the *Yersinia ruckeri* recipient strain. Since the natural Ps promoter was active in *E. coli*, it was decided to look at the expression of the original cloning plasmid in *Yersinia ruckeri*.

*Yersinia ruckeri* strain 224 was transformed by the original plasmid and shortened plasmid #12 and #18, respectively. As a control the *Yersinia ruckeri* strain 224 was also transformed by pSHVG55, a plasmid that expresses a Viral Haemorrhagic Septicaemia (VHS) antigen and is built on a replicon that has a wider host range than Col E1. This plasmid was used to see whether Col E1 replicon based plasmid was adequate for *Yersinia ruckeri*. Similarly, a European strain of *Yersinia ruckeri* was transformed with the same plasmids.

It was found that a double dose of ampicillin as compared with *E. coli* was necessary for selection. ColE1 based promoter were stable in *Yersinia ruckeri*. Yr [#18] (BCCM accession No. LMG P-22044) expressed readily detectable amount of the $^{Ps}$p45 protein.

This strain was thus, selected as a candidate vaccine. It produced the full-length $^{Ps}$p45 protein since no constructs lacking the signal peptide were available in the original cloning vectors.

Seven additional open reading frames were identified in LMG P-22044. One of these, i.e., a protein comprising SEQ ID NO: 6, encoded by SEQ ID NO: 5 shows homology with a protein family coding for AMP-binding enzymes. Two other open reading frames, i.e., a protein comprising SEQ ID NO: 8, encoded by SEQ ID NO: 7, and a protein comprising SEQ ID NO: 10, encoded by SEQ ID NO: 9, show no homology to any protein family. Yet another open reading frame i.e., a protein comprising SEQ ID NO: 12, encoded by SEQ ID NO: 11, shows homology to the DDE endonuclease family and in particular to the integrase core domain. Still another open reading frame i.e., a protein comprising SEQ ID NO: 14, encoded by SEQ ID NO: 13 shows homology to transposases. Yet another open reading frame i.e., a protein comprising SEQ ID NO: 16, encoded by SEQ ID NO: 15 shows some homology to the HlyD family of secretory proteins. Still another open reading frame i.e., a protein comprising SEQ ID NO: 18, encoded by SEQ ID NO: 17 shows homology to the intergral membrane AcrB/AcrD/AcrB protein family.

An alternative antigen, from the original cloning vector, clone #7, and a *Yersinia ruckeri*, Yr [#7] (BCCM accession No. LMG P-22511) was selected as second vaccine candidate.

Vaccine production: Each vaccine strain was grown in a 25 ml conical flask with ampicillin until mid-log phase of growth. The culture was then made 50% glycerol, aliquoted in 2 ml cryotubes to form a seed. For each vaccine, three conical 2 liter flasks containing 333 ml of Tryptone Soya Broth (TSB) plus ampicillin were inoculated with one tube of seed and grown for 36 hours with shaking at 25° C. After 36 hours, the cultures were inactivated with formaldehyde at 25° C. with agitation. Samples for quality control were taken prior to inactivation since it is known that formaldehyde causes the polymerisation of the proteins, and therefore, SDS-PAGE can't be performed on inactivated vaccines. After 24 hours the inactivation formaldehyde was neutralized with sodium bisulfite and the sterility test was performed. The vaccine was aliquoted in two one-liter bottles, each containing 500 mls of vaccine. The vaccine was released after the completion of the sterility test.

Control: As a control a formaldehyde inactivated *Yersinia ruckeri* strain 224 was cultured. The control culture had an optical density at 600 nm ($OD_{600}$ nm) of 6.0 at the time of harvest, corresponding to approx. $6 \times 10^9$ cells/ml.

BCCM accession No. LMG P-22044: (Yr[#18], expressing the $^{Ps}$p45 protein). The BCCM accession No. LMG P-22044 culture had an $OD_{600\,nm}$ 5.8 at time of harvest, corresponding to approx. $5.8 \times 10^9$ cells/ml. The expression of the $^{Ps}$p45 protein was studied in the supernatant and the cells. The recombinant $^{Ps}$p45 protein was efficiently excreted in the culture broth, it was also present in a cell associated form.

BCCM accession No. LMG P-22511: (Yr[#7]). BCCM accession No. LMG P-22511 culture had an $OD_{600\,nm}$ 5.1 at the time of harvest, corresponding to approximately $5.1 \times 10^9$ cells/ml. The expression of potential antigenic proteins from this recombinant *Yersinia ruckeri* strain was studied in the supernatant and the cells.

Example 2

Large Scale Production of *Yersinia ruckeri* (45 Liter Culture)

The bacterial strains: The recombinant strains of *Yersinia ruckeri* constitutively express antigens from *Piscirickettsia salmonis*. The vector is pGEM5ZF+ and the promoter is the natural promoter for the respective antigen from *Piscirickettsia salmonis*.

*Yersinia ruckeri* (Yr[#18] BCCM accession No. LMG P-22044 (expresses the $^{Ps}$p45 protein).

*Yersinia ruckeri* (Yr[#7]) BCCM accession No. LMG P-22511.

Seed culture: 50-100 µl of the above stock bacterial strains ("glycerol" stock) were used to inoculate 500 mls of YES medium (see below) and 100 mg/l ampicillin in a 2-liter shake-flask. The cultures were incubated at: 20-25° C., with an agitation of 270 rpm for 21 hours (+/−2 hours) and grown to have a final OD(600 nm) of between 1.5-3.0.

Fermentation: A seed culture (see above) was used to inoculate 45 liters of YES medium in a 50-liter sterilized, fermentor in order to reach an initial optical density at 600 nm of 0.002.

Culture Conditions pH=7 (10% $HNO_3$ and 4M NaOH)
Temperature=20° C.
Air-flow=45 l/min
Dissolved oxygen=30% with action on the stirring speed
Agitation=150 rpm and more if needed Pressure=3 psigs The end of the exponential growth occurs after approximately 24 hours. After 2 hours of the end of the exponential growth phase, the pH regulation is turned off and formaldehyde (37%) is added in the fermentor at a concentration of 5 ml per liter of culture in order to kill the cells. The culture is homogenised (5 minutes) and harvested in a Nalgene tank. Then, the fermentor is rapidly rinsed and sterilised (20 min, 121° C.).

Once the fermentor is sterilized, the culture is transferred to the fermentor in which inactivation proceeds by stirring gently (i.e., at 100 rpm). The temperature is controlled at 20° C., without aeration and without pH regulation. The inactivation kinetics indicate that the inactivation requires at least 6 hours of incubation with formaldehyde. Routinely the total duration for the incubation with formaldehyde is about 19 hours.

After this incubation, a sterile 1 M phosphate buffer pH 7 (3.4 liters per 45 liters of culture) is added to prepare the inactivation of the formaldehyde (15 minutes). The fermentor is mixed gently (100 rpm) and a concentrated solution of metabisulfite (final concentration 3 g/l of culture) is introduced aseptically in the fermentor (15 minutes). The homogenised inactivated culture is transferred aseptically in a sterile Nalgene tank and stored at 4° C.

| YES Medium (sterilised 20 min. at 121° C.): | |
|---|---|
| YES medium | Concentration |
| Yeast extract | 30 g/l |
| NaCl | 5 g/l |

| Solution of 1M Phosphate pH 7 (sterilised by filtration with 0.2 μm pore membrane) | |
|---|---|
| Buffer | Quantities for 1.35 liter |
| KH$_2$PO$_4$ | 53 g |
| K$_2$HPO$_4$ | 167 g |

Quality Control

Viable count (CFU) determination at the end of the fermentation

Western blot at the end of the fermentation

Sterility of the final bulk (Eur Ph protocol, 20 ml of sample—21 days)

Determination of the residual concentration of formaldehyde in the final bulk (<=500 ppm, Eur Ph protocol B)

| Production Timing | | |
|---|---|---|
| Day 1 | Preparation of the fermentor | |
| | Inoculation of the shake flask | |
| Day 2 | Inoculation of the fermentor | |
| Day 3 | Inactivation with formaldehyde | |
| | Sterilisation of the fermentor for the inactivation | |
| Day 4 | Addition of the phosphate buffer | |
| | Addition of the metabisulfite | |
| | Storage in Nalgene tank | |

Example 3

Production Method of VP2var or VP3 (50 Liter Scale)

The yeast strains: *Pichia pastoris* GS115-pPICZαB-VP2var.

The *Pichia* expression system was used to express the IPN protein antigens [Research Corporation Technologies, Tucson, Ariz., see U.S. Pat. Nos. 4,808,537, 4,837,148, 4,879, 231].

Preculture: A 2-liter baffled shake-flask containing 400 ml of YSG+ (see below) is inoculated with 600 μl of the above-identified yeast strain. The culture is incubated at 30° C., with an agitation of 270 rpm, during 23-25 hours. The optical density at 600 nm ($OD_{600\ nm}$) is >15 units (using a NOVASPEC II spectrophotometer).

Composition of the Medium YSG+:

| COMPONENTS | CONCENTRATION |
|---|---|
| Yeast Extract | 6 g/l |
| Papaïc Soy Pepton | 5 g/l |
| Glycerol | 20 g/l |

Fermentation: The fermentor Braun D50 is prepared with 50 liters of growth medium (SAPPEY, see below). The fermentor is inoculated with a volume (V) of preculture determined by the equation:

$$V_{preculture}\ (\text{ml}) = V\ \text{fermentor}\ (\text{ml}) \times 0.05 / OD_{600preculture}$$

Parameters for Fermentation

| PARAMETERS | SET POINTS |
|---|---|
| pH | 6* |
| Temperature | 30° C. |
| Air-flow | 80 l/min. |
| $PO_2$ | 30%** |
| Agitation | 400-(600) rpm |
| Pressure | 100 mbar |

*regulation with acid ($HNO_3$ 10%) and base ($NH_4OH$ 12.5%)
**with an action on the agitation to maintain the $PO_2$ at 30% Automatic regulation of foam with SAG471.

Composition of Growth Medium SAPPEY per 1 Liter:

| Components | Volumes |
|---|---|
| Base solution | 900 ml |
| Complement solution 1 | 100 ml |
| PTM1 solution | 4.76 ml |

Quantities per 1 Liter of Base Solution
[The solution is autoclaved in the fermentor (20 min., 121° C.)]

| Components | Quantity |
|---|---|
| Yeast Extract | 11.11 g/l |
| Papaic Soy Pepton | 22.22 g/l |
| Antifoam SAG471 | 0.11 ml/l |

| Quantities per 1 Liter of COMPLEMENT SOLUTION 1 (The solution is sterilised by filtration with a 0.22 μm pore membrane) | |
|---|---|
| Components | Quantity |
| $K_2HPO_4$ | 23 g/l |
| $KH_2PO_4$ | 118 g/l |
| Glycerol | 100 g/l |

| Quantity for 1 Liter of PTM1 SOLUTION | |
|---|---|
| Components | Quantity |
| $CuSO_4 \cdot 5H_2O$ | 6 g/l |
| NaI | 0.08 g/l |
| $MnSO_4 \cdot H_2O$ | 3 g/l |
| $Na_2MoO_4 \cdot 2H_2O$ | 0.2 g/l |
| $H_3BO_3$ | 0.02 g/l |
| $CoCl_2 \cdot 6H_2O$ | 0.92 g/l |
| $ZnCl_2$ | 20 g/l |
| $FeSO_4 \cdot 7H_2O$ | 65 g/l |
| d-biotine | 0.2 g/l |
| $H_2SO_4$ | 5 ml/l |

The solution is sterilized by filtration with a 0.22 μm pore membrane. The PTM1 solution must be added in the fermentor separately from the complement solution 1.

| Composition of "INDUCTION SOLUTIONS" per 1 Liter (The methanol is added by sterile filtration with a 0.22 μm pore membrane) | |
|---|---|
| Components | Volumes |
| Methanol 100% | 6.3 ml/l of culture |
| Yeast Extract solution | 22.5 ml/l of culture |

| Quantity for 1 Liter of YEAST EXTRACT SOLUTION [This solution is autoclaved (20 min., 121° C.)] | |
|---|---|
| Components | Quantity |
| Yeast Extract | 222 g/l |

After 24 hours of growth, a first induction of recombinant protein expression is realized by the addition of methanol and yeast extract solution. At this moment, the $OD_{600\ nm}$ is greater than about 10 units. After the induction the $pO_2$ decreases quickly. After about 1 hour, it increases slowly to saturation. A second induction is realized after 48 hours of culture in the same conditions. The $OD_{600\ nm}$ reached is greater than about 13 units. After 72 hours of growth, the fermentor is cooled to a temperature lower than 20° C. The $OD_{600\ nm}$ reached is greater than about 13 units.

Harvest and filling: The cells from the fermentor are then harvested. The culture is centrifuged (5000 g, 4° C., 20 min) in order to eliminate the pellets. The supernatant is aseptically filtrated with a 0.2 μm pore membrane (Sartobran P) and 2.5 liter aliquots are placed into one gallon bottles. These bottles are then stored at −20° C.

Example 4

An Injectable SRS Vaccine

Summary

One SRS injectable vaccine of the present invention is a water-in-oil type vaccine. It contains a suspension of two bacterins comprising antigens of *Piscirickettsia salmonis*, recombinant strains of *Yersinia ruckeri* of BCCM accession No. LMG P-22511, along with BCCM accession No. LMG P-22044, in phosphate buffer saline. The oily adjuvant is MONTANIDE ISA711 (obtained from SEPPIC, Paris, France) and constitutes 70% of the vaccine's total volume.

The formulation may also contain residual quantities of formaldehyde, derived from inactivation of the recombinant *Yersinia ruckeri* cultures. The SRS vaccine is designed and recommended for administration by intraperitoneal injection, at a dosage of 0.1 ml per fish, to prevent salmonid rickettsial septicaemia caused by *Piscirickettsia salmonis* in fish, more particularly salmonids, and even more particularly, in salmon.

Presentation

The SRS injectable vaccine is presented in 500 ml high density polyethylene infusion flasks closed with red rubber stoppers and having aluminum seals. The bottles and stoppers comply with the requirements of the relevant monographs of the European Pharmacopoeia (Ph. Eur). The containers are autoclaved at 121° C. for 20 minutes. The stoppers are autoclaved at 121° C. for 60 minutes.

Production

Production of Antigens of *Piscirickettsia salmonis*: Recombinant strains of *Yersinia ruckeri* of BCCM accession No. LMG P-22511, as well as BCCM accession No. LMG P-22044 are prepared as described in Examples 1 and 2 above. The stocks of work seed are thawed and inoculated in 500 ml of primary Tryptone Soya Broth (TSB) seed culture medium plus ampicillin in 2-liter flasks.

A purity test is carried out. The seed culture is incubated for around 20 hours, with gentle agitation, and is then inoculated in 18 liters of TSB fermentation medium in a 30 liter fermentor and is incubated, with agitation, until just before the end of the exponential phase indicated by optical density readings.

A viable count test is carried out. Just before the end of the exponential phase, the culture is harvested and inactivated with 37% formalin. The culture is transferred to a separate sterile container while inactivation occurs.

Samples are taken for Quality Control tests relating to sterility, inactivation, viable counts, Western Blots, residual formaldehyde content and pH.

Storage

The inactivated cultures are poured into sterile 50 liter nalgene bottles and are stored at a 4° C. until the results of the quality control tests are available.

Mixing of the Final Vaccine

Bulk antigens are mixed with phosphate buffer saline and the oily component in order to obtain a bulk vaccine of the desired cell concentration.

Filling

After completing a subsequent sterility test, the vaccine is transferred to 500 ml high density polyethylene bottles with nitrile rubber stoppers and plastic seals. The samples are tested for sterility.

Materials

Antigens: The product contains two bacterins as indicated above containing antigens of *Piscirickettsia salmonis*, isolated from the Atlantic salmon in Chile. Pure cultures of the organisms were multiplied and the DNA extracted from them was used to prepare a gene pool. The appropriate genes responsible for the expression of the antigens were inserted into separate cultures of *Yersinia ruckeri*. Since the antigens are expressed in the cell membrane, the product includes inactivated cultures of complete cells of *Y. ruckeri* in order to provide the antigens (see Examples 1 and 2 above, for more details).

TABLE 2

Reagents

| REAGENT | COMPONENTS | cHARACTERISTICS |
|---|---|---|
| Tryptone *Soya* Broth (TSB) | Pancreatic casein digestive enzyme | Cow's milk from herds certified BSE free, originally from France, but currently from New Zealand. Porcine enzymes from France, Italy and Holland. |
| | Soya digestive papain | No materials of biological origin |
| | Sodium chloride | |
| | Hydrogenated dipotassium phosphate | |
| | Dextrose | Synthetic or of non-animal origin |
| | Purified water | Meets the requirements of the European Pharmacopoeia. |
| Hydrochloric acid (pH adjustment) | — | Meets the requirements of the European Pharmacopoeia. |
| Sodium hydroxide (pH adjustment) | — | Meets the requirements of the European Pharmacopoeia. |
| Formaldehyde (Inactivator) | — | Meets the requirements of the European Pharmacopoeia. |
| Saline solution (Diluent) | Sodium chloride | Meets the requirements of the European Pharmacopoeia. |
| | Purified water | Meets the requirements of the European Pharmacopoeia. |
| Montanide ISA711 (Adjuvant) | Contains oleic acid | EDQM Certified available |

Validation

Equipment and Installations: The antigens are produced in an installation that operates according to international Good Manufacturing Principles (GMP) and Good Laboratory Practices (GLP). The finished vaccine is produced in accordance with international GMP. The filling process is carried out under Class 1A conditions. The environmental and HEPA laminar flow filters are subject to regular validation. Environmental supervision of the process is carried out. The filling procedure itself is validated by means of culture assays.

Manufacturing Procedure: The SRS vaccine manufacturing process involves conventional microbiological cultures in glass bottles and fermentors. The former corresponds to established procedures that do not require specific validation and the latter have been validated following installation.

Bovine Spongiform Encephalopathy: There is no evidence that fish can transmit or host spongiform encephalopathies (TSEs). However, the sources of materials of biological origin used in the manufacture of the vaccines of the present invention are inspected with respect to the potential transmission of spongiform encephalopathies. It is considered that the risks of spongiform encephalopathies being spread by the use of the vaccines of the present invention are minimal if any.

Assays

Several tests are carried out to ensure that the consistency and quality of the vaccine and its components are maintained. These tests are described below.

Seed Culture: A purity test is carried out by spreading the culture on plates of agar jelly. The acceptance criterion is a pure culture.

Culture On Harvest (Viability count): There are no set limits. The number of CFU/ml is recorded for mixing purposes.

Inactivated Antigens: A sterility test is carried out in accordance with the Ph. Eur. The acceptance criterion is that the culture must be sterile. The sterility test has also served as inactivation test, with the acceptance criterion being no growth. The residual formaldehyde test described in the Ph. Eur. is carried out solely to determine the amount.

pH: The pH is measured using a pH meter. The range is normally pH 6.5±0.5

Mixed Vaccine: A sterility test is carried out in accordance with the Ph. Eur., with the acceptance criterion being that the culture must be sterile.

Tests on Full Containers: A sterility test is carried out in accordance with the Ph. Eur. Again, the acceptance criterion is that the culture must be sterile.

Safety In Target Species: A test is carried out to confirm that the vaccine is safe in the target species. This forms part of the experimental program.

Stability: Stability tests are carried out on the finished product. The program of stability tests includes tests on the product at the time of manufacture and following storage for 15 and 27 months at temperatures of between 2° C. and 8° C. Particular attention is paid to the product's appearance and the potency of the antigens it contains.

Example 5

An Injectable Vaccine for SRS and IPN

Summary

One injectable vaccine of the present invention is a water-in-oil type vaccine. This vaccine contains a suspension of two recombinant proteins (VP2 and VP3) or antigenic fragments thereof from Infectious Pancreatic Necrosis virus and bacterins comprising antigens of *Piscirickettsia salmonis* in recombinant strains of *Yersinia ruckeri* of BCCM accession No. LMG P-22511, along with BCCM accession No. LMG P-22044, in phosphate buffer saline.

Antigenic fragments of each of the two IPN recombinant proteins are included in the vaccine. VP2 (VP2var) recombinant proteins are expressed by transformed yeast, *Pichia pastors* BCCM Accession No. IHEM 20069 and/or BCCM Accession No. IHEM 20070, whereas VP3 recombinant proteins are expressed by BCCM Accession No. IHEM 20071 and/or BCCM Accession No. IHEM 20072. The oily adjuvant is MONTANIDE ISA711 and constitutes 70% of the vaccine's total volume. The formulation may contain residual amounts of formaldehyde, derived from inactivation of the cultures.

This particular vaccine is designed and recommended for administration by intraperitoneal injection, to protect against salmonid rickettsial septicaemia, and infectious pancreatic necrosis in fish, more particularly salmonids, and even more particularly, in salmon.

Presentation

The injectable vaccine for SRS and IPN is presented in 500 ml high density polyethylene infusion flasks, closed with red rubber stoppers and having aluminum seals. The bottles and stoppers comply with the requirements of the relevant monographs of the European Pharmacopoeia (Ph. Eur). The containers are autoclaved at 121° C. for 20 minutes. The stoppers are autoclaved at 121° C. for 60 minutes.

Production

Production of Antigens of IPNV

A container of work seed is opened and inoculated in 400 ml of medium and is incubated at approximately 30° C. for 19-24 hours. The culture is inoculated in 46 to 47 liters of growth medium in a fermentor. The pH is adjusted to pH 6.0 with hydrochloric acid or sodium hydroxide. The culture is incubated at approximately 30° C. for 24 hours. Under continuous fermentation, methanol and yeast extract is added to induce protein expression, and this is repeated 24 hours later. Following incubation for a total of 72 hours, the fermentor is cooled to below 20° C. Then the cells are eliminated by centrifuging and discarded in compliance with local environmental protection regulations. The supernatant containing the expressed protein is sterilized by filtration (0.22 μm pore membrane) and stored at −20° C. until it is required for mixing.

Production of Antigens of *Piscirickettsia salmonis*: Recombinant strains of *Yersinia ruckeri* of BCCM accession No. LMG P-22511, and BCCM accession No. LMG P-22044 are prepared and stored as described in Example 4 above.

A purity test is carried out. The seed culture is incubated for around 20 hours, with gentle agitation. The culture is next inoculated in 18 liters of TSB fermentation medium in a 30 liter fermentor and then incubated, with agitation, until just before the end of the exponential phase, as indicated by optical density readings.

A viable count test is carried out. Just before the end of the exponential phase, the culture is harvested and inactivated with 37% formalin. The culture is transferred to a separate sterile container while inactivation occurs.

Samples are taken for Quality Control tests relating to sterility, inactivation, viable count, Western blot, residual formaldehyde content and pH.

Storage

The inactivated cultures are poured into sterile 50 liter nalgene bottles and are stored at a 4° C. until the results of the quality control tests are available.

Mixing of the Final Vaccine

Bulk antigens are mixed with the other antigen components, phosphate-buffered saline solution, and the oil component to obtain a bulk vaccine of the desired cell concentration.

The volumes of bulk antigens required (calculated on the individual concentrations of bulk antigen, the required concentrations of these in the end product and the batch size) are removed from storage. The bulk antigens are transferred to cool, sterile containers and are mixed thoroughly.

The volume of sterile saline required is calculated and transferred aseptically to the mixed bulk antigens. The antigens and saline are thoroughly mixed and the pH is adjusted to pH 7.0-7.4 with 10 M sodium hydroxide or 10 M hydrochloric acid (aqueous phase).

The weight of sterile oily phase required is calculated and transferred aseptically to a sterile mixing container. The oily and aqueous phases are emulsified for 5 minutes at approximately 3000 rpm. The emulsified mix is maintained at ambient temperature for 24 hours. The mix is placed in the final containers, with a nominal fill value of 505 ml. The stoppers are inserted aseptically and the seals are applied. Each container is labeled, packaged and stored at +2° C. to +8° C. under quarantine until released for sale. The batch size varies according to production requirements and is normally within the range of 100 liters to 1500 liters.

Validation

Equipment, Installations and manufacturing procedure: Validation of the equipment, installations and manufacturing procedure is as described in Example 4 above.

Materials

*Piscirickettsia salmonis* Antigens: The product contains two bacterins as indicated above containing antigens of *Piscirickettsia salmonis*, isolated from the Atlantic salmon in Chile. Pure cultures of the organisms were multiplied and the DNA extracted from them was used to prepare a gene pool. The appropriate genes responsible for the expression of the antigens were inserted into separate cultures of *Yersinia ruckeri*. Since the antigens are expressed in the cell membrane, the product includes inactivated cultures of complete cells of *Y. ruckeri* in order to provide the antigens (see Examples 1, 2 and 4 above, for more details).

The vaccine also contains recombinant proteins VP2 var and VP3 of IPNV [see WO 02/38770 A1] to protect against the IPN virus. The VP2 var protein used is derived from a strain of IPN virus known as Sp.

VP2var is a region of the VP2 protein previously identified as a variable segment of VP2 that comprises about 150 amino acid residues [previously identified as amino acids 183-337 encoded by nucleotides 678-1140, see, Havarstein et al., *J. Gen. Virol.* 71:299-308 (1990); Pryde et al., *Archives of Vir.* 129:287-293 (1992)].

Nucleic acids encoding VP3 and VP2 var have been cloned and inserted in the *Pichia pastoris* yeast. The yeast engineering method is such that the relevant gene sequences are integrated in the host's genome and there is no free plasmid present.

The IPN virus from which the cloned gene sequences derive was originally isolated from sick Atlantic salmon on a salmon farm in the Shetland Islands [see WO 02/38770 A1, the contents of which are hereby incorporated by reference in their entireties].

Other Reagents are provided in Table 2 of Example 4 above.

Bovine Spongiform Encephalopathy: There is no evidence that fish can transmit or host spongiform encephalopathies (TSEs). For further detail see Example 4 above.

Assays

Several tests are carried out to ensure that the consistency and quality of the vaccine and its components are maintained. These tests are described below.

For the IPN Proteins:

Purity

The purity of the specific work seed inoculant used is verified by examining the culture plate to confirm that the colonies formed are typical and consistent and that no colony with contaminating organisms is present. The acceptance criterion is that all colonies must be of similar appearance and be typical of *Pichia pastoris.*

Sterility

This assay is performed on a sample of the material harvested soon after the mixing of the bulk antigens but prior to mixing with the oily phase. The test is designed to demonstrate sterility of the material and specifically to check that there are no *Pichia pastoris* cells present.

The method used is that described by the Ph. Eur. 1 ml of harvested sample is inoculated in each of two tubes containing 9 ml of Thioglycollate Broth or Soya Bean Broth. The tubes are incubated at 32° C. and 22° C. respectively for 14 days. Those tubes that do not show any growth during this period are subcultivated for a further 7 days. Positive and negative controls are included in all tests. All tubes and plates that are inoculated only with the test sample must not show any growth, whereas all tubes and plates that are inoculated with the positive control organisms must show growth of the control organism. In addition to the normal tests to confirm the sterility of the medium, the method has been specifically approved in order to demonstrate that the technique is capable of revealing live *Pichia pastoris*. This study demonstrated that as few as 2-3 cells in the sample produce a profuse growth within 5 days of incubation.

SDS-PAGE

A sample of each harvest is tested by SDS-PAGE to confirm that the expected proteins have been produced. The samples are separated using a 15% acrylamide gel. Two identical gels are used for each sample, one treated with Coomassie Brilliant Blue to stain the proteins and the other Western Blotted on nitrocellulose which is then immunoblotted with specific monoclonal anti-VP2 and anti-VP3 antibodies. The stained gels must show bands of protein in the correct molecular weight position (30 kDa for VP3 and 42 kDa for VP2 var). These bands must correspond specifically to bands recognised by the corresponding monoclonal antibodies.

Protein Content

A test for protein concentration in the harvested material is performed to provide a quantitative estimate of yield and to form the basis for the final mixing of the vaccine. The method used employs Coomassie Blue to bind the protein and bovine serum albumin (BSA) as the protein standard. No specific criterion applies since the test is designed solely to provide a quantitative result. However, the normal range of protein concentration in the harvest is approximately 10-50 mg/ml. It is anticipated that the yield may vary in the case of larger-scale production, and it may then be appropriate to apply a specific criterion.

For the *Piscirickettsia salmonis* Antigens:

The assays carried out to ensure that the consistency and quality of these components are maintained are described in Example 4 above.

Assay of the Finished Product

A sterility test is carried out in accordance with the Ph. Eur. with the acceptance criterion being that the culture is sterile. A sterility test of the Full Containers comprising the vaccine is carried out in accordance with the Ph. Eur. with the acceptance criterion being that the culture is sterile.

A test is also carried out to confirm that the vaccine is safe in the target species. This forms part of the experimental program.

Finally, stability tests are carried out on the finished product. The stability test program includes tests on the product at the time of manufacture and following storage for 15 and 27 months at temperatures between 2° C. and 8° C. Particular attention is paid to the product's appearance and potency of the antigens it contains.

Example 6

An Injectable Vaccine for SRS, IPN and Furunculosis

Summary

One injectable vaccine of the present invention is a water-in-oil type vaccine that comprises a suspension of:

(i) two inactivated strains of *Aeromonas salmonicida* (MT004 and MT423), (ii) two recombinant IPN viral proteins (VP2 and VP3) or antigenic fragments thereof, that are expressed by transformed yeast, *Pichia pastoris* in 0.85% p/v sterile saline, and (iii) a suspension comprising inactivated recombinant strains of *Yersinia ruckeri* that comprise antigens from *Piscirickettsia salmonis*, having the BCCM accession No. LMG P-22511, along with BCCM accession No. LMG P-22044, in phosphate buffered saline.

The VP2 (VP2var) recombinant proteins are expressed by transformed yeast, *Pichia pastoris* BCCM Accession No. IHEM 20069 and/or BCCM Accession No. IHEM 20070, whereas the VP3 recombinant proteins are expressed by BCCM Accession No. IHEM 20071, and/or BCCM Accession No. IHEM 20072. The oily adjuvant is MONTANIDE ISA711 and constitutes 70% of the vaccine's total volume.

The formulation may contain residual amounts of formaldehyde, derived from inactivation of the cultures.

This particular vaccine is designed and recommended for administration by intraperitoneal injection, to protect against salmonid rickettsial septicaemia, infectious pancreatic necrosis and furunculosis in fish, more particularly salmonids, and even more particularly, in salmon.

Presentation

This vaccine is presented in 500 ml high density polyethylene infusion flasks, closed with grey nitrile stoppers and having aluminium seals. The bottles and stoppers comply with the requirements of the relevant monographs of the European Pharmacopoeia (Ph. Eur). The containers are autoclaved at 121° C. for 20 minutes. The stoppers are autoclaved at 121° C. for 60 minutes.

Production

Production of *A. salmonicida* MT004 Antigen: An ampoule of lyophilized work seed is removed from storage and is reconstituted and incubated. This culture is then inoculated in 4 liters of sterile iron-deficient TSB to form the production culture, and then incubated at approximately 21.5° C. for 36-48 hours.

The resulting culture is then aseptically inoculated in 15-18 liters of sterile iron-deficient TSB. It is incubated at approximately 21.5° C. for 24 to 48 hours. Then a solution of sterile formaldehyde is added to the flasks to inactivate the culture. Each culture is mixed vigorously following the addition of the formaldehyde solution and is then transferred aseptically to a sterile storage bottle. The culture is kept at approximately 22° C. for 96-100 hours to ensure the inactivation of bacterial cultures and protease activity. The formaldehyde is neutralized by the addition of a solution of 15% sodium metabisulfite. Neutralisation is completed in 20-24 hours at a temperature of approximately 22° C. The inactivated harvests are stored at 2-8° C. until they are required for mixing. The production of *A. salmonicida* MT004 antigen can also be performed as described below for MT423.

Production of *A. salmonicida* MT423 Antigen: An ampoule of lyophilized work seed is removed from storage and reconstituted and incubated. This culture is then inoculated in 300 ml of sterile iron-supplemented TSB to form the production culture, and then incubated at approximately 21.5° C. for 36-48 hours.

The culture is next inoculated aseptically in 4 liters of sterile iron-supplemented TSB. It is incubated at approximately 21.5° C. for 36 to 48 hours. The culture of production seed is transferred aseptically to 150 liters of sterile iron-supplemented TSB in a fermentor and incubated at approximately 21.5° C. for 20-24 hours.

Then a solution of sterile formaldehyde is added to the culture flasks to inactivate them. Each culture is mixed vigorously following the addition of the formaldehyde solution and is transferred aseptically to a sterile storage bottle. The culture is kept at approximately 22° C. for 96-100 hours to ensure inactivation of the bacterial cultures and protease activity. The formaldehyde is neutralized by adding a solution of 15% sodium metabisulfite. Neutralization is completed in 20-24 hours at a temperature of approximately 22° C. The inactivated harvests are stored at 2-8° C. until they are required for mixing Production of Recombinant Proteins IPN (VP2 VAR) and IPN VP3: Recombinant proteins IPN (VP2 VAR) and IPN VP3 are prepared and stored as described in Example 5 above.

Production of Antigens of *Piscirickettsia salmonis*: Recombinant strains of *Yersinia ruckeri* of BCCM accession No. LMG P-22511 and BCCM accession No. LMG P-22044 are prepared and stored as described in Example 4 above.

Mixing of the Final Vaccine

Mixing of the antigens to form the final vaccine is performed as described in Example 5 above.

Validation

Equipment, Installations and manufacturing procedure: Validation of the equipment, installations and manufacturing procedure is as described in Example 4 above.

Materials

*Piscirickettsia salmonis* Antigens: The product contains two bacterins as indicated above containing antigens of *Piscirickettsia salmonis*, isolated from the Atlantic salmon in Chile. Pure cultures of the organisms were multiplied and the DNA extracted from them was used to prepare a gene pool. The appropriate genes responsible for the expression of the antigens were inserted into separate cultures of *Yersinia ruckeri*. Since the antigens are expressed in the cell membrane, the product includes inactivated cultures of complete cells of *Y. ruckeri* in order to provide the antigens (see Examples 1, 2 and 4 above, for more details).

In addition two strains of *Aeromonas salmonicida* are used, which derive from isolated naturally infected fish obtained from fish farmed in Scotland. In spite of the fact that there is no evidence that there is any serological distinction between different strains of *Aeromonas salmonicida*, there is a scientific basis for including more than one strain in this vaccine. This is due to the fact that different isolated ones may be A-layer positive or negative. Considering that the presence or absence of this layer may not be directly linked to virulence, the absence of an A-layer allows greater exposure to outer membrane proteins (OMPs), and in particular, those OMPs produced only under conditions of iron restriction, as may occur during the infection process. As a result, the production and immunological availability of the iron restriction outer membrane proteins (IROMPs) is thought to be important to the efficacy of the vaccine.

*Aeromonas salmonicida* (MT004): The MT004 strain is an A-layer negative strain, which is cultivated under conditions of iron restriction. Development under these conditions results in the production of specific is iron restriction outer membrane proteins that stimulate the production of bacterial antibodies following intraperitoneal inoculation.

The strain was originally isolated from dying Atlantic salmon during an outbreak of furunculosis in on a salmon farm on the West Coast of Scotland in October 1985. It was passaged through tryptone soya broth six times and remained virulent to the host animal.

*Aeromonas salmonicida* (MT423): The MT423 strain is an A-layer positive strain that has been cultivated in a fermentor under conditions of iron supplementation. A-layer is a component of successful *A. salmonicida* vaccines and supplementation with iron has increased the protection afforded by the furunculosis vaccine.

The MT423 strain was isolated from sick Atlantic salmon from a salmon farm at Stirling University. It was passaged 16 times in Atlantic salmon and remained virulent to the host animal and is therefore appropriate for use as a vaccine strain.

Both strains are inactivated by exposure to formaldehyde, being in non-infecting organisms, whereas it retains its ability to stimulate an immune response in vaccinated fish.

The vaccine also contains the recombinant proteins VP2 var and VP3 of IPNV as described in Example 5 above.

Other Reagents are provided in Table 2 of Example 4 above.

Bovine Spongiform Encephalopathy: There is no evidence that fish can transmit or host spongiform encephalopathies (TSEs). For further detail see Example 4 above.

Assays

Several tests are carried out to ensure that the consistency and quality of the vaccine and its components are maintained. These tests are described below.

*Aeromonas salmonicida* Strains MT004 and MT423: The test methods used for both antigens are the same, except that the test for the presence of IROMPS is not used for the MT423 strain, since this is multiplied in an iron-enriched medium. In addition, the criteria used for some tests are different for each strain. For the sake of simplicity, the following test descriptions specify the criterion for each strain where it is appropriate.

Purity Tests—Gram Stain: Gram stain purity tests are carried out on each subculture during multiplication from seed to production culture. The test provides a rapid indication that the cultivated organism has the hoped for microscopic appearance and that no atypical organism is present.

The test method is a simple Gram stain that uses conventional techniques and materials. Known Gram positive and negative control organisms are stained each time to confirm that staining and discoloration are appropriate. The test sample must only show small Gram negative rods.

Purity Test and Characteristics of the Culture: An additional purity test is carried out on each of the 20 liter complete cultures and on the culture in the final fermentor. The test confirms the purity of the culture and contributes to global identity security. A sample of the culture is grown on plates of tryptone soya agar and incubated at 22° C. for at least 48 hours, long enough for the different colonies to become visible. Plates inoculated with the test culture must exhibit only one type of bacterial colony. These colonies must be typical of *Aeromonas salmonicida.*

The *Aeromonas salmonicida* MT004 strain forms semi-translucent, round, convex, cream-colored colonies with regular edges. A red-brown pigmentation is produced which spreads through the medium after around 24 hours of culture. The *Aeromonas salmonicida* MT423 strain: Semi-translucent, round, convex, cream-colored colonies with regular edges, but developing more slowly than the MT004 strain.

Identity of the culture: The identity of a given culture is confirmed in the samples on final fermentation. Identity tests are carried out on the final culture prior to inactivation to confirm that the correct organism has been cultured. It must be emphasized that none of these tests can differentiate the strains, but all contribute to the security of identifying the species. In addition to the purity tests, identity is confirmed by means of biochemical and agglutination characteristics:

Demonstration of the use of glucose without gas production.

A sample from the final culture is inoculated in peptone water containing 1% glucose and phenol red in tubes containing an inverted Durham tube. The inoculated cultures are incubated at 22° C. for 24-48 hours. The test sample must show the use of glucose, indicated by acid production, without gas being produced.

Demonstration of positive metabolism of cytochrome oxidase using commercially available impregnated filter papers:

A single colony from the purity test plate (culture characteristics) is spread over the filter paper. A positive result is indicated by the development of a pinkish purple pigment while a negative result is indicated by no color change. The cultures must generate a pinkish purple coloration on the test paper, indicating positive cytochrome oxidase metabolism.

Lattes cover-glass test using a diagnostic kit of pathogens from commercial fish (Bionor MONO-AS—Code DD020).

A single colony from the purity test plate (culture characteristics) is mixed with a drop of antiserum on a microscope slide. The test uses a specific rabbit antiserum against *Aeromonas salmonicida*. A negative control culture is likewise mixed with a drop of antiserum. Positive agglutination must be observed with the test sample. The negative control sample must not show any agglutination.

Optical Density: Optical density measurements at 580 nm are recorded at the end of each culture in 20 liter bottles and at intervals throughout final fermentation. Optical density measurements are taken from 20 liter culture bottles to ensure that each of these inoculants has grown satisfactorily. Optical density measurements are recorded at intervals throughout final fermentation to determine the optimum time for harvest, as indicated at the end of the exponential growth phase.

A sample of the culture is placed in a cuvette and the optical density is measured directly using a spectrophotometer. If necessary, the sample may be diluted in 0.85% sterile saline solution in order to obtain opacity within the spectrophotometer's range. The method is only used to confirm satisfactory growth of the inoculant and to determine the optimum time for harvest of the final fermentation. The final optical density reading is not critical and no set criterion applies. However, the final value obtained from the culture in the fermentor is normally within the following range:

8-11 for MT004 strain (without iron)

13-18 for MT423 strain (iron supplemented)

The absolute criterion for optical density is not appropriate for several reasons. First, considering that the medium used is of biological origin, there is inevitably a variation in the degree to which a specific batch will support growth. Second, the frequency of sampling for optical density is restricted to 45 minute intervals due to the need to re-sterilize the sampling port. Consequently, the precise harvest time may allow the culture to be maintained in the stationary phase for a short period of time, during which a reduction in optical density may be observed.

Viable Count

A sample of the culture is taken for the viable count at the end of fermentation and prior to adding the inactivator. The viable count serves as a definitive measurement of yield and forms the basis for subsequent mixing of the vaccine. The viable count is carried out using the Miles and Misra method [see e.g., Hedges, *Int J Food Microbiol.* 25:76(3):207-14 (2002)] with Tryptone Soya Broth as diluent and Tryptone Soya Agar as growth medium. Suitable ten-fold serial dilutions of the sample are prepared and ten replicate 0.025 ml drops of each dilution placed on the agar plate. The plates are incubated at 22° C. for 24-48 hours. Only those dilutions where colonies may be clearly counted are used to calculate the viable count.

The viable count is used as the basis for mixing the vaccine. The actual count is not critical and no set criterion is applied. However, normal counts are within the range $0.3$-$1.5 \times 10^{10}$/ml for both strains MT004 and MT423. The absolute criterion is not appropriate for several reasons. First, considering that the medium used is of biological origin, there is inevitably a variation in the degree to which a specific batch will support growth.

Second, the frequency of sampling for optical density is restricted to 45 minute intervals due to the need to re-sterilize the sampling port. Consequently, the precise harvest time may allow the culture to be maintained in the stationary phase for a short period of time, during which a reduction in optical density may be observed.

Protease Test

The protease test is carried out on a sample of material taken immediately following the inactivation period, but before the addition of sodium thiosulphate. With the improved control of the culture's conditions, no release of protease has been observed. However, because it is possible to sample the culture from the final fermentor at intervals of no less than 45 minutes, there is the possibility that some cells will die, and consequently lysis may occur prior to inactivation. This test provides the reassurance that any protease that may be released is completely inactivated.

Protease Assay: 3 ml of inactivated culture is added to 20 mg of SKY BLUE powder suspended in 2.5 ml of PBS and incubated for 15 minutes at ambient temperature. A positive control in which 20 mg of trypsin replaces the test samples is also incubated. The SKY BLUE powder is insoluble in PBS, but if protease activity is present, the material degrades and blue dye is released into the solution. The positive control must show a blue color while negative controls must remain colorless. To be acceptable, the test samples must not exhibit any protease activity. Positive samples must show a blue coloration.

Inactivation Test

A specific test for inactivation of the culture is carried out following neutralization of the residual inactivator. A subsequent test for continuous and complete inactivation is carried out on the mixed aqueous phase of the vaccine. The test confirms the complete, satisfactory inactivation of all viable organisms.

Inactivation assay: 1 ml of inactivated culture is inoculated in each of six tubes containing 9 ml of TSB. Two of these inoculated tubes are inoculated with 0.1 ml of positive control culture with *Aeromonas salmonicida* of the same strains as the sample being tested, inoculating with a designated concentration of between 1 and 10 organisms. Two further inoculated tubes are additionally inoculated with 0.1 ml using the same positive control culture diluted 1 in 10. Also 0.1 ml of both positive control preparations are inoculated in two tubes, each containing 9.9 ml of TSB and another two tubes of TSB medium are kept only as negative controls. Therefore, duplicates of the following tubes are prepared (a total of 12 tubes in all):

Inoculated with 1 ml of test sample

Inoculated with 1 ml of test sample+0.1 ml positive control

Inoculated with 1 ml of test sample+0.1 ml positive control (diluted 1/10)

Inoculated with 0.1 ml positive control

Inoculated with 0.1 ml positive control diluted 1/10

Not inoculated

All of the above tubes are incubated for 48 hours at 22° C. At the end of this time, any tube in which growth cannot be seen is subcultivated. Subcultivation is carried out by spreading 1 ml of the medium onto each of two plates of tryptone soya agar. The medium is left to absorb into the agar for 1 hour at ambient temperature and the plates are incubated (inverted) for 48 hours at 22° C. The original tubes are also incubated for 48 hours at 22° C.

At the end of this time, growth (or absence of growth) is recorded in all cultures. The criterion of being acceptable is that all the tubes inoculated with the test sample only and all plates inoculated from these must not show any growth. In addition, all tubes inoculated with the highest concentration of organisms of the positive control and/or all plates inoculated from these must show growth of the control organism. If the tubes inoculated exclusively with the lowest dilution of the positive control culture and/or the plates inoculated from these show growth, similar results must be observed for the tubes and plates inoculated with the test sample plus the diluted positive control. The control mediums must remain negative.

Test for IROMPS

This test only applies to the material of strain MT004 and applies to a sample of final bulk antigen following inactivation and neutralization but, prior to distributing the material between the storage containers. The test is a qualitative method for confirming the presence of typical iron-restricted proteins in the preparation.

SDS-PAGE electrophoresis is performed on the sample. The SDS-PAGE gels are electroblotted to PVDF membranes that are then incubated with a rat monoclonal antibody against IROMP. Coupling of the monoclonal antibody is detected by a conjugate of goat anti-rat alkaline phosphatase and displayed using a NBT-BCIP substrate. A positive control preparation of *Aeromonas salmonicida* IROMP is spread on the same gel together with the molecular weight markers. The method is qualitative, but the acceptance criterion requires that the samples exhibit bands consistent with those of the control preparation. More particularly, protein bands must be detected at about 70, 72, 77 and 82 kilodaltons.

Sterility

The sterility of each container of final bulk antigen is confirmed using a specific sterility test although the inactivation test also provides additional evidence of sterility of the bulk product prior to distribution. The test provides the assurance that each container of bulk antigen is sterile. The method used is that indicated in the Ph. Eur. Using direct inoculation thioglycollate and soya broths are incubated at 32° C. and 22° C. respectively, and both are subcultivated after 14 days of incubation. The subcultures are incubated for 7 days, while the original cultures are incubated for a total of 21 days. The method includes positive control cultures specified in the Ph. Eur.

To be acceptable the samples being tested must be sterile. The positive control cultures must show profuse early growth (within 3 days).

For the *Piscirickettsia salmonis* Antigens:

The assays carried out to ensure that the consistency and quality of these components are maintained are described in Example 4 above.

For the IPN Proteins VP2 var and VP3:

The assays carried out to ensure that the consistency and quality of these components are maintained are described in Example 5 above.

Assay of the Finished Product

The assays carried out to ensure that the sterility of the final vaccine and containers that comprise the final vaccine is maintained are described in Example 5 above. In addition, Example 5 describes the procedures regarding the safety of the vaccine in the target species, as well as its stability after storage.

Example 7

Safety and Efficacy of SRS Vaccine in Atlantic Salmon

Introduction

Atlantic salmon in Chile are subject to infection with *Piscirickettsia salmonis*. Mortality due to *P. salmonis* usually occurs between 6-12 weeks after fish are transferred to seawater cages, but outbreaks may appear in seawater up to the end of the production cycle.

Summary

Groups of 50 Atlantic salmon of average weight 50 g were vaccinated in fresh water by injection with the SRS vaccine at a dose of 0.1 ml per fish. The test was conducted using a pilot scale batch of the vaccine manufactured according to GLP, as in Example 4 above.

A control group of 50 fish were injected with 0.1 ml of phosphate buffered saline (PBS).

A sentinel unit was set up with at least 10 fish injected with each preparation as indicated above. Although there was some mortality in the sentinel unit due to poor adaptation of the fish to seawater, no additional fish died during the full period of the trial, which assured that external infection were absent in the facilities during the trial.

Safety of the vaccine was demonstrated by observing behaviour, feeding, and general condition of fish for 21 days post-vaccination for each group. No adverse reactions were observed due to the vaccine or the vaccination process.

Efficacy of the vaccine was demonstrated by challenge. At [1]540° days post vaccination (38 days post vaccination), fish were gradually transferred to seawater during three days. At 800° days post vaccination (56 days post-vaccination), fish in all groups were challenged by an intraperitoneal injection (0.1 ml/fish) using the supernatant from a *Piscirickettsia salmonis* culture (Chilean isolate) grown on CHSE-214 cells.

[1] As defined in the DETAILED DESCRIPTION above.

Mortality was recorded for 6 weeks post-challenge. Mortality in challenged control group injected with PBS was 93.8%, whereas in vaccinated fish mortalities were only 53.1%.

Relative Percent Survival (RPS) values were calculated when Cumulative Mortality in the control group was ≧60% (RPS 60), and at the end of the trial (RPS End). Vaccinated fish showed an RPS 60 of 100% and an RPS End of 43.4%.

When administered by injection in Atlantic salmon at a dose of 0.1 ml vaccine/fish, the SRS vaccine was safe and exhibited high levels of effectiveness in protecting Atlantic salmon against *Piscirickettsia salmonis* experimental infection.

The results of this study show that the SRS vaccine is safe when administrated by injection at the recommended dose. The SRS vaccine showed efficacy against experimental infections with *Piscirickettsia salmonis*.

Materials and Methods

Holding Conditions: Atlantic salmon (*Salmo salar*) weighing 50 g were held in circular tanks 1 m diameter and 60 cm depth at a flow rate of 150-200 L/hour on a standard diet. Oxygen was continuously supplied and temperature controlled at 14° C. Biomass was identical (2.5 kg fish) in all the test units except for the sentinel unit, where the biomass was 3.25 kg fish.

Fish were maintained in fresh water during 540° days after vaccination (38 days post-vaccination). Then, seawater was gradually introduced in the tanks during 3 days. Food was withdrawn for 24 hours before vaccination.

The vaccine was the oil-based injectable SRS vaccine of Example 4 above.

Acclimatization: Fish were transferred from the stock holding facility to the test aquarium facilities one week before the vaccination was due to commence to allow acclimatization. Feeding ceased at least 24 hours prior to vaccination.

Vaccination Procedure: The vaccine was administered by injection as described below: The vaccine was allowed to warm to room temperature and mixed thoroughly by vigorous shaking for two minutes prior to use. Fish were anaesthetized using benzocaine by the standard method, and 0.1 ml of the appropriate preparation was delivered intraperitoneally. There were two preparations employed, as follows, with the remaining fish (33) kept in a separate unit as sentinels.

Injection with the SRS vaccine
Injection with PBS

A total of 133 fish were included in the study.

Groups of 50 fish were vaccinated with each of the two preparations indicated above. After being injected fish from each group were distributed in five tanks, given a final number of 10 fish/group/tank.

At least 10 fish were injected with each of the preparations indicated above.

Safety Assessment: Following vaccination, fish were checked for general condition, and any adverse effects were recorded for 21 days after vaccination to assess the safety of the vaccine tested. Any mortality was observed for signs of adhesions. If any, adhesions were classified according to the Spielberg scale.

Efficacy Assessment: Following vaccination and 21-day observation for safety, fish were challenged. After challenge, behaviour, feeding, general condition, and mortality were recorded daily for 6 weeks to assess the efficacy of the vaccine.

Efficacy was defined as a comparative reduction in specific mortality due to SRS in vaccinated fish as compared to unvaccinated control groups. The reduction in mortalities was evaluated using an index of protection known as the Relative Percent Survival (R.P.S.). This is calculated as:

$$1 - \left(\left(\frac{\% \text{ Vaccinates Mortality}}{\% \text{ Control Mortality}}\right)\right) \times 100$$

Experimental Challenge: The *Piscirickettsia salmonis* strain was MHC401-2001. The strain was isolated in February 2001 from *Salmo salar* kidney tissue in Chile. Isolation and multiplication of the strain has been done on CHSE-214 cells. Experimental challenge was carried out in seawater 800° days post-vaccination (56 days post-vaccination). *Piscirickettsia salmonis* was inoculated in CHSE-214 cells (80% confluence) and incubated in MEM-5 at 15° C. for 25 days. Supernatant was collected and titered on CHSE-214 in 96-well microplates incubated at 15° C. for 14 days.

The supernatant titer was $5.99 \times 10^5$ $TCID_{50}$/ml. Fish were challenged by intraperitoneal injections at a rate of 0.1 ml of supernatant, which gave a dose per fish of $5.99 \times 10^4$ TCID.

Sampling: During the challenge, any dead fish were removed and stored frozen at −20° C. Once the trial was completed, kidney samples from any mortality post-challenge were tested for presence of *P. salmonis* in kidney by using the immunodiagnostics kit SRS ELISA commercialized by BIOSChile Ingenieria Genetica S.A.

Statistical Analysis: The fish tank was considered as a random blocking effect. The proportion of cumulative mortality for each treatment group in each tank was analyzed by mixed model ANOVA, using tank nested within the treatment group as the random effect in the model and Satterthwaite degrees of freedom. Significance tests for random variance terms were performed using the covtest option.

Statistical analysis was performed using SAS version 8.2 (SAS Institute, Cary N.C., USA) and StatXact 4.0.2 (Cytel Software Corporation, Cambridge Mass., USA) for exact confidence intervals and exact tests for differences in overall proportions for cumulative mortality. Statistical significance was declared for $p \leq 0.05$.

Results

In the sentinel unit 2 fish (out of 13) from the vaccinated group, and 4 fish (out of 20) from the control group died two days after transfer to seawater, but no mortality occurred in the trial units.

| SAFETY OF THE SRS VACCINE | | | |
|---|---|---|---|
| TREATMENT | MORTALITY | % MORTALITY | REMARKS |
| SRS vaccine | 1/50 | 2 | No adhesions |
| PBS | 1/50 | 2 | No adhesions |

Only one fish in the vaccinated group and one in the PBS control group died during the 21 days after vaccination. The mortality occurred 7 days post-vaccination and no adhesions were observed in any of the fish.

Efficacy of vaccine: As the tank was not found to be a significant effect in the model, differences in cumulative percent mortality and tests for significance were included for overall mortality percentages, mortality pooled over all replicates (tanks).

Mortality due to SRS began 9 days post-challenge in the PBS control group, and 15 days post-challenge in the vaccinated group (see FIG. 1 below).

Differences for cumulative mortality percentages between vaccine and the PBS-injected control group were statistically significant at the 60% mortality time point, and at the end of the study (p<0.0021).

Efficacy was defined as a comparative reduction in specific mortality due to SRS in fish given injection vaccination with the SRS vaccine as compared to unvaccinated control groups. Relative Percent Survival (R.P.S.) was calculated when the cumulative mortality in the control group was $\geq 60\%$ (R.P.S. 60), and at the end of the trial (R.P.S. End):

| R.P.S. 60 | | | |
|---|---|---|---|
| TREATMENT | MORTALITY | % MORTALITY | R.P.S. |
| SRS vaccine | 0/49 | 0.0 | 100 |
| PBS | 32/48 | 66.7 | — |

| R.P.S. End | | | |
|---|---|---|---|
| TREATMENT | MORTALITY | % MORTALITY | R.P.S. |
| SRS vaccine | 26/49 | 53.1 | 43.4 |
| PBS | 45/48 | 93.8 | — |

SRS Diagnostics: The immunodiagnostics kit SRS ELISA commercialised by BIOSChile Ingenieria Genetica S.A. was used to assess the presence of *P. salmonis* in the kidneys of the challenged fish.

| ELISA | SRS Vaccine | PBS |
|---|---|---|
| Positive | 12/26 | 17/45 |
| Suspected positive | 3/26 | 4/45 |
| Negative | 11/26 | 24/45 |

Discussion

No significant mortalities occurred in the vaccinated group during the vaccination process or in the following 21 days after vaccination. Vaccinated fish showed the same level of mortality as the PBS control group. In addition, no adhesions were observed. These results indicate that the SRS vaccine is safe when administered by injection at a dose of 0.1 ml vaccine/fish in Atlantic salmon.

The data generated by using the ELISA test kits (BIOSChile Ingenieria Genetica) needs to be interpreted with some care. Almost 50% of the vaccinated mortalities checked for *P. salmonis* with the ELISA kits in kidney were positive for SRS, while almost 40% were positive in the control mortalities. In both groups, vaccinated and control fish, approximately 10% of the samples were suspected positive. This leaves a remainder of between 40-50% of the mortality, which were negative for presence of *P. salmonis* in kidney. There is no evidence of any other infection in the units, as was proved by the sentinel unit. The negative kidneys could be due to several factors, such as sensitivity of the test, that the level of kidney infection which was enough to kill the fish but not high enough to be detected by the test, or that the infectious agent deteriorated in the frozen samples and was less easy to detect.

The conclusion, given that the distribution of positive, suspected positive, and negative tests is approximately the same in all groups of fish in the trial, and the fact that the sentinel groups were unaffected, is that the cause of mortality in the experiment is SRS. The data was analysed on this basis.

Vaccination with the SRS vaccine delayed the occurrence of infection by *P. salmonis* when compared with the PBS injected fish. Relative Percent Survival in the vaccinated fish was 100% when the control mortality was $\geq 60\%$, whereas at the end of the trial R.P.S. for the vaccinated group was 43.4%. The results indicate that SRS was effective in reducing mortality from *P. salmonis* infection when fish were vaccinated by injection with 0.1 ml vaccine/fish.

Example 8

Safety and Efficacy of SRS/IPN Vaccine in Atlantic Salmon

Summary

The identical study as that disclosed in Example 7 above was performed except the vaccine also contained IPN antigens.

Mortality was recorded for 6 weeks post-challenge. Mortality in the challenged control group injected with PBS was 93.8%, whereas in the vaccinated fish the mortalities was 65.2%. Relative Percent Survival (RPS) values were calculated when Cumulative Mortality in the control group was $\geq 60\%$ (RPS 60), and at the end of the trial (RPS End). Vaccinated fish showed an RPS 60 of 93.6% and an RPS End of 30.5%.

The SRS/IPN vaccine was safe when administered at a dose of 0.1 ml vaccine/fish by injection to Atlantic salmon, and exhibits high levels of effectiveness in protecting Atlantic salmon against *Piscirickettsia salmonis* experimental infection.

The results of this study show that the combined SRS and IPN vaccine is safe when administered by injection at the recommended dose. Moreover, the SRS/IPN vaccine showed efficacy against experimental infections with *Piscirickettsia salmonis*.

Materials and Methods

The holding conditions, Atlantic salmon, acclimatization, vaccination procedure, safety assessment, efficacy assessment, experimental challenge, sampling, and statistical analysis were all identical to those described in Example 7 above.

The vaccine was the oil-based injectable SRS/IPN vaccine of Example 5 above, containing the IPN antigens deposited as BCCM Accession No. IHEM 20069 and BCCM Accession No. IHEM 20071, respectively.

Results

In the sentinel unit 3 fish (out of 13) from the vaccinated group, and 4 fish (out of 20) from the control group died two days after transfer to sea water, but no mortality occurred in the trial units.

| SAFETY of SRS/IPN VACCINE | | | |
|---|---|---|---|
| TREATMENT | MORTALITY | % MORTALITY | REMARKS |
| SRS/IPN vaccine | 0/50 | 0 | — |
| PBS | 1/50 | 2 | No adhesions |

None of the fish in the vaccinated group, and only one fish in the PBS control group died during the 21 days after vaccination. The mortality in the control group occurred 7 days post-vaccination.

Figure 2:
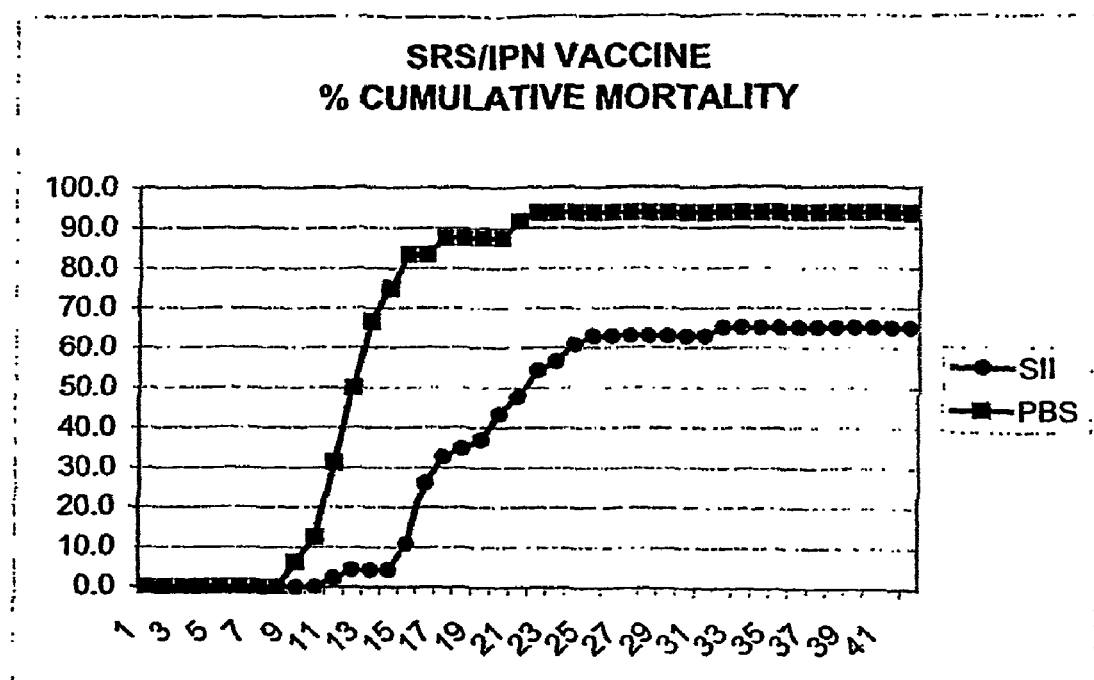
FIG. 2 shows the mortality due to SRS began 9 days post-challenge in the PBS control group, and 11 days post-challenge in the SRS/IPN vaccinated group (see Example 8 below).

Efficacy of the SRS/IPN Vaccine: As the tank was not found to be a significant effect in the model, differences in cumulative percent mortality and tests for significance were included for overall mortality percentages, mortality pooled over all replicates (tanks), Mortality due to SRS began 9 days post-challenge in the PBS control group, and 11 days post-challenge in the vaccinated group (see FIG. 2 below).

Differences for cumulative mortality percentages between vaccine and the PBS-injected control group were statistically significant at the 60% mortality time point, and at the end of the study (p<0.0171).

Efficacy was defined as a comparative reduction in specific mortality due to SRS in fish given injection vaccination with the combined SRS/IPN vaccine as compared to unvaccinated control groups. Relative Percent Survival (R.P.S.) was calculated when the cumulative mortality in the PBS control group was $\geq 60\%$ (R.P.S. 60), and at the end of the trial (R.P.S. End):

| R.P.S. 60 | | | |
|---|---|---|---|
| TREATMENT | MORTALITY | % MORTALITY | R.P.S. |
| SRS/IPN Vaccine | 2/46 | 4.3 | 93.6 |
| PBS | 32/48 | 66.7 | — |

| R.P.S. End | | | |
|---|---|---|---|
| TREATMENT | MORTALITY | % MORTALITY | R.P.S. |
| SRS/IPN Vaccine | 30/46 | 65.2 | 30.5 |
| PBS | 45/48 | 93.8 | — |

SRS Diagnostics: The immunodiagnostics kit SRS ELISA commercialised by BIOSChile Ingenieria Genetica S.A. was used to assess the presence of *P. salmonis* in the kidneys of the challenged fish.

| ELISA | SRS/IPN Vaccine | PBS |
|---|---|---|
| Positive | 16/30 | 17/45 |
| Suspected positive | 3/30 | 4/45 |
| Negative | 11/30 | 24/45 |

Discussion

No mortalities occurred in the vaccinated group during the vaccination process or in the following 21 days after vaccination, which indicates that SRS/IPN vaccine of the present invention is safe when administrated by injection at a dose of 0.1 ml vaccine/fish in Atlantic salmon.

The data generated by using the ELISA test kits (BIOSChile Ingenieria Genetica) needs to be interpreted with some care. More than 50% of the vaccinated mortalities checked for *P. salmonis* with the ELISA kits in kidney were positive for SRS, while almost 40% were positive in the control mortalities. In both groups, vaccinated and control fish, approximately 10% of the samples were suspected positive. This leaves a remainder of between 40-50% of the mortality, which were negative for presence of *P. salmonis* in kidney. There is no evidence of any other infection in the units, as was proved by the sentinel unit. The negative kidneys could be due to several factors, such as sensitivity of the test, that the level of kidney infection which was enough to kill the fish but not high enough to be detected by the test, or that the infectious agent deteriorated in the frozen samples and was less easy to detect.

Vaccination with the SRS/IPN vaccine slightly delayed the occurrence of infection by *P. salmonis* relative to the PBS injected fish. Relative Percent Survival in the vaccinated fish was 93.6% when PBS control mortality was ≧60%, whereas at the end of the trial R.P.S. for the vaccinated group was 30.5%. The results indicate that the SRS/IPN vaccine was effective in reducing mortality from *P. salmonis* infection when fish were vaccinated by injection with 0.1 ml vaccine/fish.

TABLE 3

SEQUENCES

| SEQ ID NO.: | DESCRIPTION |
|---|---|
| 1 | Nucleotide sequence encoding the 45 kDa protein. |
| 2 | Amino acid sequence of the 45 kDa protein. |
| 3 | Nucleotide sequence encoding the 45 kDa protein minus the signal peptide. |
| 4 | Amino acid sequence of the 45 kDa protein minus the signal peptide. |
| 5 | Nucleotide sequence encoding an AMP binding enzyme homolog. |
| 6 | Amino acid sequence of an AMP binding enzyme homolog. |
| 7 | Nucleotide sequence encoding ORF A. |
| 8 | Amino acid sequence of ORF A. |
| 9 | Nucleotide sequence encoding ORF B. |

TABLE 3-continued

SEQUENCES

| SEQ ID NO.: | DESCRIPTION |
|---|---|
| 10 | Amino acid sequence of ORF B. |
| 11 | Nucleotide sequence encoding a DDE endonuclease homolog. |
| 12 | Amino acid sequence of a DDE endonuclease homolog. |
| 13 | Nucleotide sequence encoding a transposase homolog. |
| 14 | Amino acid sequence of a transposase homolog. |
| 15 | Nucleotide sequence encoding an HlyD homolog. |
| 16 | Amino acid sequence of an HlyD homolog. |
| 17 | Nucleotide sequence encoding an AcrB/AcrD/AcrF homolog. |
| 18 | Amino acid sequence of an AcrB/AcrD/AcrF homolog. |
| 19 | 2,092 nucleotide nucleic acid sequence comprising the coding sequence of the 45 kDa protein. |

The present invention is not to be limited in scope by the specific embodiments describe herein. Indeed, various modifications of the invention in addition to those described herein will become apparent to those skilled in the art from the foregoing description. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. An isolated recombinant *Piscirickettsia salmonis* 45 Kda ($^{Ps}$p45) polypeptide comprising the amino acid sequence of SEQ ID NO: 2 or SEQ ID NO: 4.

2. The isolated recombinant polypeptide of claim 1 that is a chimeric protein.

3. An immunogenic composition that comprises the isolated recombinant $^{Ps}$p45 polypeptide of claim 1.

4. The immunogenic composition of claim 3 further comprising an antigen obtained from an Infectious Pancreatic Necrosis (IPN) virus, wherein the antigen obtained from the IPN virus is selected from the group consisting of a VP2 var protein, a VP3 protein, and a combination thereof.

5. The immunogenic composition of claim 4 wherein the VP2 var protein is obtained from a transformed *Pichia pastoris* cell, BCCM Accession No. IHEM 20069 and the VP3 protein is obtained from a transformed *Pichia pastoris* cell, BCCM Accession No. IHEM 20071.

6. The immunogenic composition of claim 4 wherein the VP2 var protein is obtained from a transformed *Pichia pastoris* cell, BCCM Accession No. IHEM 20070 and the VP3 protein is obtained from a transformed *Pichia pastoris* cell, BCCM Accession No. IHEM 20072.

7. The immunogenic composition of claim 4 that further comprises an antigen obtained from *Aeromonas salmonicida*.

8. A method of protecting a salmonid fish from salmonid rickettsial septicemia comprising administering to the fish the immunogenic composition of claim 3.

9. An isolated recombinant polypeptide that comprises at least 95% of the amino acid sequence of SEQ ID NO: 2 or SEQ ID NO: 4.

10. An isolated recombinant polypeptide comprising the amino acid sequence of SEQ ID NO: 2 or SEQ ID NO: 4 with a conservative amino acid substitution.

11. The isolated recombinant polypeptide of claim 10 wherein the conservative amino acid substitution is selected from the group consisting of:

(1) a substitution of Lys for Arg;

(2) a substitution of Arg for Lys;

(3) a substitution of Glu for Asp;

(4) a substitution of Asp for Glu;

(5) a substitution of Ser for Thr;

(6) a substitution of Thr for Ser;

(7) a substitution of Gln for Asn;

(8) a substitution of Asn for Gln;

(9) a substitution of Ile for Leu

(10) a substitution of Ile for Val;

(11) a substitution of Leu for Ile; and

(12) a substitution of Leu for Val.

12. An isolated or recombinant nucleic acid encoding a $^{Ps}$p45 recombinant polypeptide, wherein the isolated or recombinant nucleic acid comprises the nucleotide sequence of SEQ ID NO: 1 or SEQ ID NO: 3.

13. An expression vector, comprising the nucleic acid of claim 12, and a transcriptional control sequence, wherein the nucleic acid is operatively linked to the transcriptional control sequence.

14. An isolated host cell that comprises the expression vector of claim 13.

15. A method for producing a $^{Ps}$p45 recombinant polypeptide comprising culturing the host cell of claim 14 in a culture medium, wherein the host cell expresses the nucleic acid encoding the recombinant $^{Ps}$p45 polypeptide; and whereby the recombinant $^{Ps}$p45 polypeptide is produced.

16. The method of claim 15 wherein the host cell is an *E. coli* cell.

17. A method of obtaining an isolated recombinant $^{Ps}$p45 polypeptide comprising purifying the recombinant polypeptide produced by the method of claim 16 from the culture medium.

18. The isolated recombinant $^{Ps}$p45 polypeptide obtained by the method of claim 17.

19. A recombinant *Yersinia ruckeri* cell comprising the expression vector of claim 13.

20. The recombinant *Yersinia ruckeri* cell of claim 19 that has the BCCM accession No. of LMG P-22044.

21. An immunogenic composition comprising the recombinant *Yersinia ruckeri* cell of claim 20.

22. The immunogenic composition of claim 21, wherein said recombinant *Yersinia ruckeri* cell is a bacterin.

23. An immunogenic composition comprising the recombinant *Yersinia ruckeri* cell of claim 19.

24. The immunogenic composition of claim 23, wherein said recombinant *Yersinia ruckeri* cell is a bacterin.

25. An immunogenic composition that comprises the expression vector of claim 13.

26. A method of protecting a salmonid fish from salmonid rickettsial septicemia comprising administering to the fish the immunogenic composition of claim 25.

27. An isolated or recombinant nucleic acid encoding a $^{Ps}$p45 recombinant polypeptide comprising the amino acid sequence of SEQ ID NO: 2 or SEQ ID NO: 4.

28. An expression vector, comprising the nucleic acid of claim 27, and a transcriptional control sequence, wherein the nucleic acid is operatively linked to the transcriptional control sequence.

29. An isolated host cell that comprises the expression vector of claim 28.

30. The isolated host cell of claim 29 wherein the host cell is an *E. coli* cell.

31. An immunogenic composition that comprises the expression vector of claim 28.

32. A method of protecting a salmonid fish from salmonid rickettsial septicemia comprising administering to the fish the immunogenic composition of claim 31.

33. The immunogenic composition of claim 31 further comprising an antigen obtained from an Infectious Pancreatic Necrosis (IPN) virus, wherein the antigen obtained from the IPN virus is selected from the group consisting of a VP2 var protein, a VP3 protein, and a combination thereof.

34. The immunogenic composition of claim 33 wherein the VP2 var protein is obtained from a transformed *Pichia pastoris* cell, BCCM Accession No. IHEM 20070 and the VP3 protein is obtained from a transformed *Pichia pastoris* cell, BCCM Accession No. IHEM 20072.

35. The immunogenic composition of claim 33 wherein the VP2 var protein is obtained from a transformed *Pichia pastoris* cell, BCCM Accession No. IHEM 20069 and the VP3 protein is obtained from a transformed *Pichia pastoris* cell, BCCM Accession No. IHEM 20071.

36. The immunogenic composition of claim 33 that further comprises an antigen obtained from *Aeromonas salmonicida*.

* * * * *

SEQUENCE LISTING

```
<160> NUMBER OF SEQ ID NOS: 19

<210> SEQ ID NO 1
<211> LENGTH: 1314
<212> TYPE: DNA
<213> ORGANISM: Piscirickettsia salmonis
<220> FEATURE:
<221> NAME/KEY: CDS
<222> LOCATION: (1)..(1314)

<400> SEQUENCE: 1 atg aaa gta aaa atg att gtt gca gct gta gct gtt gca ggt tta aca        48
Met Lys Val Lys Met Ile Val Ala Ala Val Ala Val Ala Gly Leu Thr
1               5                   10                  15 gcg act gcc gca aat gcc gct gat aat ggt aag ctt caa tta caa atc        96
Ala Thr Ala Ala Asn Ala Ala Asp Asn Gly Lys Leu Gln Leu Gln Ile
                20                  25                  30 aac caa ttg aag gcg caa cac act caa ctt caa cag caa gtt gct aat       144
Asn Gln Leu Lys Ala Gln His Thr Gln Leu Gln Gln Gln Val Ala Asn
            35                  40                  45 ctg caa ggt caa ggc caa act act ggt gcc gtt cac gtt ggc gct gtt       192
Leu Gln Gly Gln Gly Gln Thr Thr Gly Ala Val His Val Gly Ala Val
        50                  55                  60 ggt ggt gaa cta atc tct gaa aat aac tac gat ggt cgt ggc tta gat       240
Gly Gly Glu Leu Ile Ser Glu Asn Asn Tyr Asp Gly Arg Gly Leu Asp
65                  70                  75                  80 ctt ctt aaa tca tta gcg aaa gca ggc agc aat gca ccg tta tta act       288
Leu Leu Lys Ser Leu Ala Lys Ala Gly Ser Asn Ala Pro Leu Leu Thr
                85                  90                  95 att ggt ggt acg tta gaa gct gat gcg caa atg aac cgt aac ggt aat       336
```

```
                Ile Gly Gly Thr Leu Glu Ala Asp Ala Gln Met Asn Arg Asn Gly Asn
                                100                 105                 110 gtt gga tct ggt tct act tct ggt gac cct tct ggc ctt aac tat act           384
Val Gly Ser Gly Ser Thr Ser Gly Asp Pro Ser Gly Leu Asn Tyr Thr
            115                 120                 125 gat gga act agc agt tct gca ttc tat tta gat act gca cgt att gat           432
Asp Gly Thr Ser Ser Ser Ala Phe Tyr Leu Asp Thr Ala Arg Ile Asp
            130                 135                 140 atc tta gcg cat gtg aat gac tgg gtt aac ggt gaa atc tcg tat gac           480
Ile Leu Ala His Val Asn Asp Trp Val Asn Gly Glu Ile Ser Tyr Asp
145                 150                 155                 160 tta aat ggt gat agt ggt ctt cac act ggt agc ctt tta gtg ggt aac           528
Leu Asn Gly Asp Ser Gly Leu His Thr Gly Ser Leu Leu Val Gly Asn
                165                 170                 175 ctc aat caa tta cca gtt tat ggt caa atc ggt aaa ttc tac cca gat           576
Leu Asn Gln Leu Pro Val Tyr Gly Gln Ile Gly Lys Phe Tyr Pro Asp
            180                 185                 190 gca ggt ttg ttt gaa tta gct agt gat gat gtt tat tct tct agc tta           624
Ala Gly Leu Phe Glu Leu Ala Ser Asp Asp Val Tyr Ser Ser Ser Leu
            195                 200                 205 gtc aag cgt tat ttc cgt cca gat gcg caa aat ggt gca tct gta ggc           672
Val Lys Arg Tyr Phe Arg Pro Asp Ala Gln Asn Gly Ala Ser Val Gly
210                 215                 220 ttc tat aaa gca ggc tta cat act tct tta act gca ttt aaa acg tct           720
Phe Tyr Lys Ala Gly Leu His Thr Ser Leu Thr Ala Phe Lys Thr Ser
225                 230                 235                 240 gct cca caa gct aat gct gct aac tat aac caa gca act agt gat tgg           768
Ala Pro Gln Ala Asn Ala Ala Asn Tyr Asn Gln Ala Thr Ser Asp Trp
                245                 250                 255 tct gca caa gcg gat tac act ttt aat gca ggt caa gtc aat gcc act           816
Ser Ala Gln Ala Asp Tyr Thr Phe Asn Ala Gly Gln Val Asn Ala Thr
            260                 265                 270 ata ggt gca ggt tac tta tct aat atg gtg aat acc aat gac agc ttc           864
Ile Gly Ala Gly Tyr Leu Ser Asn Met Val Asn Thr Asn Asp Ser Phe
            275                 280                 285 act gca aca ggt gca gga act ggt aca caa aaa gat cgg cta ccg atg           912
Thr Ala Thr Gly Ala Gly Thr Gly Thr Gln Lys Asp Arg Leu Pro Met
            290                 295                 300 gct aat gta agc gct aag att ggc ttt ggt cca ttt gaa gcc ctt gct           960
Ala Asn Val Ser Ala Lys Ile Gly Phe Gly Pro Phe Glu Ala Leu Ala
305                 310                 315                 320 act tat gct caa aca tta aaa ggt ttg gcg aat act aca ggt ggt aca          1008
Thr Tyr Ala Gln Thr Leu Lys Gly Leu Ala Asn Thr Thr Gly Gly Thr
                325                 330                 335 acg aag ttg aaa gcc ttt gat tta gaa ggt gct tac cac ttc caa gct          1056
Thr Lys Leu Lys Ala Phe Asp Leu Glu Gly Ala Tyr His Phe Gln Ala
            340                 345                 350 gtg aag ccg atg act gtg atg tta ggt tat agc cgt aca tat ggc ttt          1104
Val Lys Pro Met Thr Val Met Leu Gly Tyr Ser Arg Thr Tyr Gly Phe
            355                 360                 365 gat aag gtt gga cct gtt gat cag ttt att gat ggt aat act gcg att          1152
Asp Lys Val Gly Pro Val Asp Gln Phe Ile Asp Gly Asn Thr Ala Ile
            370                 375                 380 act atc aat aac aaa aaa gac caa tgg tta ttg ggt gta aac tct gaa          1200
Thr Ile Asn Asn Lys Lys Asp Gln Trp Leu Leu Gly Val Asn Ser Glu
385                 390                 395                 400 gta ttt aag aac aca acg gtt ggt ctt gag tat gcg cgt gta ggt cag          1248
Val Phe Lys Asn Thr Thr Val Gly Leu Glu Tyr Ala Arg Val Gly Gln
                405                 410                 415
```

```
ctt gat agc aca ggt act gac act aac cgc tac aac gta ttg act gcg    1296
Leu Asp Ser Thr Gly Thr Asp Thr Asn Arg Tyr Asn Val Leu Thr Ala
        420                 425                 430 gat atg act gtt aag ttc                                            1314
Asp Met Thr Val Lys Phe
        435
```

<210> SEQ ID NO 2
<211> LENGTH: 438
<212> TYPE: PRT
<213> ORGANISM: Piscirickettsia salmonis

<400> SEQUENCE: 2

```
Met Lys Val Lys Met Ile Val Ala Ala Val Ala Val Ala Gly Leu Thr
1               5                   10                  15

Ala Thr Ala Ala Asn Ala Ala Asp Gly Lys Leu Gln Leu Gln Ile
            20                  25                  30

Asn Gln Leu Lys Ala Gln His Thr Gln Leu Gln Gln Val Ala Asn
        35                  40                  45

Leu Gln Gly Gln Gly Gln Thr Thr Gly Ala Val His Val Gly Ala Val
 50                  55                  60

Gly Gly Glu Leu Ile Ser Glu Asn Asn Tyr Asp Gly Arg Gly Leu Asp
 65                  70                  75                  80

Leu Leu Lys Ser Leu Ala Lys Ala Gly Ser Asn Ala Pro Leu Leu Thr
                85                  90                  95

Ile Gly Gly Thr Leu Glu Ala Asp Ala Gln Met Asn Arg Asn Gly Asn
            100                 105                 110

Val Gly Ser Gly Ser Thr Ser Gly Asp Pro Ser Gly Leu Asn Tyr Thr
        115                 120                 125

Asp Gly Thr Ser Ser Ser Ala Phe Tyr Leu Asp Thr Ala Arg Ile Asp
    130                 135                 140

Ile Leu Ala His Val Asn Asp Trp Val Asn Gly Glu Ile Ser Tyr Asp
145                 150                 155                 160

Leu Asn Gly Asp Ser Gly Leu His Thr Gly Ser Leu Leu Val Gly Asn
                165                 170                 175

Leu Asn Gln Leu Pro Val Tyr Gly Gln Ile Gly Lys Phe Tyr Pro Asp
            180                 185                 190

Ala Gly Leu Phe Glu Leu Ala Ser Asp Val Tyr Ser Ser Ser Leu
        195                 200                 205

Val Lys Arg Tyr Phe Arg Pro Asp Ala Gln Asn Gly Ala Ser Val Gly
    210                 215                 220

Phe Tyr Lys Ala Gly Leu His Thr Ser Leu Thr Ala Phe Lys Thr Ser
225                 230                 235                 240

Ala Pro Gln Ala Asn Ala Ala Asn Tyr Asn Gln Ala Thr Ser Asp Trp
                245                 250                 255

Ser Ala Gln Ala Asp Tyr Thr Phe Asn Ala Gly Gln Val Asn Ala Thr
            260                 265                 270

Ile Gly Ala Gly Tyr Leu Ser Asn Met Val Asn Thr Asn Asp Ser Phe
        275                 280                 285

Thr Ala Thr Gly Ala Gly Thr Gly Thr Gln Lys Asp Arg Leu Pro Met
    290                 295                 300

Ala Asn Val Ser Ala Lys Ile Gly Phe Gly Pro Phe Glu Ala Leu Ala
305                 310                 315                 320

Thr Tyr Ala Gln Thr Leu Lys Gly Leu Ala Asn Thr Thr Gly Gly Thr
                325                 330                 335
```

```
            Thr Lys Leu Lys Ala Phe Asp Leu Glu Gly Ala Tyr His Phe Gln Ala
                            340                 345                 350

Val Lys Pro Met Thr Val Met Leu Gly Tyr Ser Arg Thr Tyr Gly Phe
                        355                 360                 365

Asp Lys Val Gly Pro Val Asp Gln Phe Ile Asp Gly Asn Thr Ala Ile
                    370                 375                 380

Thr Ile Asn Asn Lys Lys Asp Gln Trp Leu Leu Gly Val Asn Ser Glu
            385                 390                 395                 400

Val Phe Lys Asn Thr Thr Val Gly Leu Glu Tyr Ala Arg Val Gly Gln
                            405                 410                 415

Leu Asp Ser Thr Gly Thr Asp Thr Asn Arg Tyr Asn Val Leu Thr Ala
                        420                 425                 430

Asp Met Thr Val Lys Phe
                        435

<210> SEQ ID NO 3
<211> LENGTH: 1248
<212> TYPE: DNA
<213> ORGANISM: Piscirickettsia salmonis
<220> FEATURE:
<221> NAME/KEY: CDS
<222> LOCATION: (1)..(1248)

<400> SEQUENCE: 3 gct gat aat ggt aag ctt caa tta caa atc aac caa ttg aag gcg caa       48
Ala Asp Asn Gly Lys Leu Gln Leu Gln Ile Asn Gln Leu Lys Ala Gln
1               5                   10                  15 cac act caa ctt caa cag caa gtt gct aat ctg caa ggt caa ggc caa       96
His Thr Gln Leu Gln Gln Gln Val Ala Asn Leu Gln Gly Gln Gly Gln
            20                  25                  30 act act ggt gcc gtt cac gtt ggc gct gtt ggt ggt gaa cta atc tct      144
Thr Thr Gly Ala Val His Val Gly Ala Val Gly Gly Glu Leu Ile Ser
        35                  40                  45 gaa aat aac tac gat ggt cgt ggc tta gat ctt ctt aaa tca tta gcg      192
Glu Asn Asn Tyr Asp Gly Arg Gly Leu Asp Leu Leu Lys Ser Leu Ala
    50                  55                  60 aaa gca ggc agc aat gca ccg tta tta act att ggt ggt acg tta gaa      240
Lys Ala Gly Ser Asn Ala Pro Leu Leu Thr Ile Gly Gly Thr Leu Glu
65                  70                  75                  80 gct gat gcg caa atg aac cgt aac ggt aat gtt gga tct ggt tct act      288
Ala Asp Ala Gln Met Asn Arg Asn Gly Asn Val Gly Ser Gly Ser Thr
                85                  90                  95 tct ggt gac cct tct ggc ctt aac tat act gat gga act agc agt tct      336
Ser Gly Asp Pro Ser Gly Leu Asn Tyr Thr Asp Gly Thr Ser Ser Ser
            100                 105                 110 gca ttc tat tta gat act gca cgt att gat atc tta gcg cat gtg aat      384
Ala Phe Tyr Leu Asp Thr Ala Arg Ile Asp Ile Leu Ala His Val Asn
        115                 120                 125 gac tgg gtt aac ggt gaa atc tcg tat gac tta aat ggt gat agt ggt      432
Asp Trp Val Asn Gly Glu Ile Ser Tyr Asp Leu Asn Gly Asp Ser Gly
    130                 135                 140 ctt cac act ggt agc ctt tta gtg ggt aac ctc aat caa tta cca gtt      480
Leu His Thr Gly Ser Leu Leu Val Gly Asn Leu Asn Gln Leu Pro Val
145                 150                 155                 160 tat ggt caa atc ggt aaa ttc tac cca gat gca ggt ttg ttt gaa tta      528
Tyr Gly Gln Ile Gly Lys Phe Tyr Pro Asp Ala Gly Leu Phe Glu Leu
                165                 170                 175 gct agt gat gat gtt tat tct tct agc tta gtc aag cgt tat ttc cgt      576
Ala Ser Asp Asp Val Tyr Ser Ser Ser Leu Val Lys Arg Tyr Phe Arg
            180                 185                 190
```

```
cca gat gcg caa aat ggt gca tct gta ggc ttc tat aaa gca ggc tta     624
Pro Asp Ala Gln Asn Gly Ala Ser Val Gly Phe Tyr Lys Ala Gly Leu
            195                 200                 205 cat act tct tta act gca ttt aaa acg tct gct cca caa gct aat gct     672
His Thr Ser Leu Thr Ala Phe Lys Thr Ser Ala Pro Gln Ala Asn Ala
        210                 215                 220 gct aac tat aac caa gca act agt gat tgg tct gca caa gcg gat tac     720
Ala Asn Tyr Asn Gln Ala Thr Ser Asp Trp Ser Ala Gln Ala Asp Tyr
225                 230                 235                 240 act ttt aat gca ggt caa gtc aat gcc act ata ggt gca ggt tac tta     768
Thr Phe Asn Ala Gly Gln Val Asn Ala Thr Ile Gly Ala Gly Tyr Leu
                245                 250                 255 tct aat atg gtg aat acc aat gac agc ttc act gca aca ggt gca gga     816
Ser Asn Met Val Asn Thr Asn Asp Ser Phe Thr Ala Thr Gly Ala Gly
            260                 265                 270 act ggt aca caa aaa gat cgg cta ccg atg gct aat gta agc gct aag     864
Thr Gly Thr Gln Lys Asp Arg Leu Pro Met Ala Asn Val Ser Ala Lys
        275                 280                 285 att ggc ttt ggt cca ttt gaa gcc ctt gct act tat gct caa aca tta     912
Ile Gly Phe Gly Pro Phe Glu Ala Leu Ala Thr Tyr Ala Gln Thr Leu
290                 295                 300 aaa ggt ttg gcg aat act aca ggt ggt aca acg aag ttg aaa gcc ttt     960
Lys Gly Leu Ala Asn Thr Thr Gly Gly Thr Thr Lys Leu Lys Ala Phe
305                 310                 315                 320 gat tta gaa ggt gct tac cac ttc caa gct gtg aag ccg atg act gtg    1008
Asp Leu Glu Gly Ala Tyr His Phe Gln Ala Val Lys Pro Met Thr Val
                325                 330                 335 atg tta ggt tat agc cgt aca tat ggc ttt gat aag gtt gga cct gtt    1056
Met Leu Gly Tyr Ser Arg Thr Tyr Gly Phe Asp Lys Val Gly Pro Val
            340                 345                 350 gat cag ttt att gat ggt aat act gcg att act atc aat aac aaa aaa    1104
Asp Gln Phe Ile Asp Gly Asn Thr Ala Ile Thr Ile Asn Asn Lys Lys
        355                 360                 365 gac caa tgg tta ttg ggt gta aac tct gaa gta ttt aag aac aca acg    1152
Asp Gln Trp Leu Leu Gly Val Asn Ser Glu Val Phe Lys Asn Thr Thr
370                 375                 380 gtt ggt ctt gag tat gcg cgt gta ggt cag ctt gat agc aca ggt act    1200
Val Gly Leu Glu Tyr Ala Arg Val Gly Gln Leu Asp Ser Thr Gly Thr
385                 390                 395                 400 gac act aac cgc tac aac gta ttg act gcg gat atg act gtt aag ttc    1248
Asp Thr Asn Arg Tyr Asn Val Leu Thr Ala Asp Met Thr Val Lys Phe
                405                 410                 415
```

<210> SEQ ID NO 4
<211> LENGTH: 416
<212> TYPE: PRT
<213> ORGANISM: Piscirickettsia salmonis

<400> SEQUENCE: 4

```
Ala Asp Asn Gly Lys Leu Gln Leu Gln Ile Asn Gln Leu Lys Ala Gln
1               5                   10                  15

His Thr Gln Leu Gln Gln Gln Val Ala Asn Leu Gln Gly Gln Gly Gln
            20                  25                  30

Thr Thr Gly Ala Val His Val Gly Ala Val Gly Gly Glu Leu Ile Ser
        35                  40                  45

Glu Asn Asn Tyr Asp Gly Arg Gly Leu Asp Leu Leu Lys Ser Leu Ala
    50                  55                  60

Lys Ala Gly Ser Asn Ala Pro Leu Leu Thr Ile Gly Gly Thr Leu Glu
65                  70                  75                  80
```

```
Ala Asp Ala Gln Met Asn Arg Asn Gly Asn Val Gly Ser Gly Ser Thr
                85                  90                  95

Ser Gly Asp Pro Ser Gly Leu Asn Tyr Thr Asp Gly Thr Ser Ser Ser
            100                 105                 110

Ala Phe Tyr Leu Asp Thr Ala Arg Ile Asp Ile Leu Ala His Val Asn
        115                 120                 125

Asp Trp Val Asn Gly Glu Ile Ser Tyr Asp Leu Asn Gly Asp Ser Gly
    130                 135                 140

Leu His Thr Gly Ser Leu Leu Val Gly Asn Leu Asn Gln Leu Pro Val
145                 150                 155                 160

Tyr Gly Gln Ile Gly Lys Phe Tyr Pro Asp Ala Gly Leu Phe Glu Leu
                165                 170                 175

Ala Ser Asp Asp Val Tyr Ser Ser Leu Val Lys Arg Tyr Phe Arg
            180                 185                 190

Pro Asp Ala Gln Asn Gly Ala Ser Val Gly Phe Tyr Lys Ala Gly Leu
        195                 200                 205

His Thr Ser Leu Thr Ala Phe Lys Thr Ser Ala Pro Gln Ala Asn Ala
    210                 215                 220

Ala Asn Tyr Asn Gln Ala Thr Ser Asp Trp Ser Ala Gln Ala Asp Tyr
225                 230                 235                 240

Thr Phe Asn Ala Gly Gln Val Asn Ala Thr Ile Gly Ala Gly Tyr Leu
                245                 250                 255

Ser Asn Met Val Asn Thr Asn Asp Ser Phe Thr Ala Thr Gly Ala Gly
            260                 265                 270

Thr Gly Thr Gln Lys Asp Arg Leu Pro Met Ala Asn Val Ser Ala Lys
    275                 280                 285

Ile Gly Phe Gly Pro Phe Glu Ala Leu Ala Thr Tyr Ala Gln Thr Leu
290                 295                 300

Lys Gly Leu Ala Asn Thr Thr Gly Gly Thr Thr Lys Leu Lys Ala Phe
305                 310                 315                 320

Asp Leu Glu Gly Ala Tyr His Phe Gln Ala Val Lys Pro Met Thr Val
                325                 330                 335

Met Leu Gly Tyr Ser Arg Thr Tyr Gly Phe Asp Lys Val Gly Pro Val
            340                 345                 350

Asp Gln Phe Ile Asp Gly Asn Thr Ala Ile Thr Ile Asn Asn Lys Lys
        355                 360                 365

Asp Gln Trp Leu Leu Gly Val Asn Ser Glu Val Phe Lys Asn Thr Thr
    370                 375                 380

Val Gly Leu Glu Tyr Ala Arg Val Gly Gln Leu Asp Ser Thr Gly Thr
385                 390                 395                 400

Asp Thr Asn Arg Tyr Asn Val Leu Thr Ala Asp Met Thr Val Lys Phe
                405                 410                 415

<210> SEQ ID NO 5

<400> SEQUENCE: 5

000

<210> SEQ ID NO 6

<400> SEQUENCE: 6

000
```

-continued

<210> SEQ ID NO 7
<400> SEQUENCE: 7
000

<210> SEQ ID NO 8
<400> SEQUENCE: 8
000

<210> SEQ ID NO 9
<400> SEQUENCE: 9
000

<210> SEQ ID NO 10
<400> SEQUENCE: 10
000

<210> SEQ ID NO 11
<400> SEQUENCE: 11
000

<210> SEQ ID NO 12
<400> SEQUENCE: 12
000

<210> SEQ ID NO 13
<400> SEQUENCE: 13
000

<210> SEQ ID NO 14
<400> SEQUENCE: 14
000

<210> SEQ ID NO 15
<400> SEQUENCE: 15
000

<210> SEQ ID NO 16
<400> SEQUENCE: 16
000

<210> SEQ ID NO 17
<400> SEQUENCE: 17
000

<210> SEQ ID NO 18

<400> SEQUENCE: 18

000

<210> SEQ ID NO 19
<211> LENGTH: 2092
<212> TYPE: DNA
<213> ORGANISM: Piscirickettsia salmonis

<400> SEQUENCE: 19

| | | | | | |
|---|---|---|---|---|---|
| ccaagaacta | tcaaaaacta | tataggcaaa | gtataaagtc | tgaagcttaa | cctttgctta | 60 |
| aatgtacatc | aggcttaagg | tgatttctgt | tgagtatttt | cagagtctta | agctcaattt | 120 |
| aatctttctt | aaggttgaaa | acaggctaaa | atcaacattt | tgataaaatt | attaattttt | 180 |
| ttttattgtt | cttttttaat | cggttttat | cctaatttga | tagatagtta | tcgaaattca | 240 |
| ataagttttg | tttttaattg | aattttttt | acgagtttgg | gttttacaaa | gtgaatttac | 300 |
| ctggttatag | tagccccagt | tgcttaatag | cacttaaatg | tgtatccaga | taaaaacaag | 360 |
| ttagggtaaa | aagaatgaaa | gtaaaaatga | ttgttgcagc | tgtagctgtt | gcaggtttaa | 420 |
| cagcgactgc | cgcaaatgcc | gctgataatg | gtaagcttca | attacaaatc | aaccaattga | 480 |
| aggcgcaaca | cactcaactt | caacagcaag | ttgctaatct | gcaaggtcaa | ggccaaacta | 540 |
| ctggtgccgt | tcacgttggc | gctgttggtg | gtgaactaat | ctctgaaaat | aactacgatg | 600 |
| gtcgtggctt | agatcttctt | aaatcattag | cgaaagcagg | cagcaatgca | ccgttattaa | 660 |
| ctattggtgg | tacgttagaa | gctgatgcgc | aaatgaaccg | taacggtaat | gttggatctg | 720 |
| gttctacttc | tggtgaccct | tctggcctta | actatactga | tggaactagc | agttctgcat | 780 |
| tctatttaga | tactgcacgt | attgatatct | tagcgcatgt | gaatgactgg | gttaacggtg | 840 |
| aaatctcgta | tgacttaaat | ggtgatagtg | gtcttcacac | tggtagcctt | ttagtgggta | 900 |
| acctcaatca | attaccagtt | tatggtcaaa | tcggtaaatt | ctacccagat | gcaggtttgt | 960 |
| ttgaattagc | tagtgatgat | gtttattctt | ctagcttagt | caagcgttat | ttccgtccag | 1020 |
| atgcgcaaaa | tggtgcatct | gtaggcttct | ataaagcagg | cttacatact | tctttaactg | 1080 |
| catttaaaac | gtctgctcca | caagctaatg | ctgctaacta | taaccaagca | actagtgatt | 1140 |
| ggtctgcaca | agcggattac | acttttaatg | caggtcaagt | caatgccact | ataggtgcag | 1200 |
| gttacttatc | taatatggtg | aataccaatg | acagcttcac | tgcaacaggt | gcaggaactg | 1260 |
| gtacacaaaa | agatcggcta | ccgatggcta | atgtaagcgc | taagattggc | tttggtccat | 1320 |
| ttgaagccct | tgctacttat | gctcaaacat | taaaaggttt | ggcgaatact | acaggtggta | 1380 |
| caacgaagtt | gaaagccttt | gatttagaag | gtgcttacca | cttccaagct | gtgaagccga | 1440 |
| tgactgtgat | gttaggttat | agccgtacat | atggctttga | taaggttgga | cctgttgatc | 1500 |
| agtttattga | tggtaatact | gcgattacta | tcaataacaa | aaaagaccaa | tggttattgg | 1560 |
| gtgtaaactc | tgaagtattt | aagaacacaa | cggttggtct | tgagtatgcg | cgtgtaggtc | 1620 |
| agcttgatag | cacaggtact | gacactaacc | gctacaacgt | attgactgcg | gatatgactg | 1680 |
| ttaagttcta | atttaagaac | tttaaagttt | tcaaaaaggc | gctgcggcgc | cttttttat | 1740 |
| gggcgttaat | tattggtaat | gtaggctagt | atttaaattt | gtgagtgatg | agagatgaaa | 1800 |
| aatttaatct | atgcacagcg | tttgctttat | tttgccgtat | tgattgcggt | gattgtcacc | 1860 |

```
tttgttcagc catttctaat gccgattaag cttgctgatg tgcctttaat gccgctcgtg    1920
gtcgcttcga tttattcctt gattttgct gcagctttag cattagctgc atataaatta    1980
ccgagcaaag ctggttggcc gcggtttttg ttggtgattt tatttattgg ggatgcgatg    2040
cctgcggtaa aaaactggct agtgctttgg catacgacgg agcttttgc ga             2092
```